(12) United States Patent
Porter et al.

(10) Patent No.: US 9,844,211 B2
(45) Date of Patent: Dec. 19, 2017

(54) MMTV-SV40-SPY1A AND SPY1A-PTRE TRANSGENIC MOUSE MODELS

(71) Applicants: Lisa Porter, Amherstburg (CA);
Bre-Anne Fifield, Windsor (CA);
Dorota Lubanska, Windsor (CA);
Espanta Jalili, Windsor (CA)

(72) Inventors: Lisa Porter, Amherstburg (CA);
Bre-Anne Fifield, Windsor (CA);
Dorota Lubanska, Windsor (CA);
Espanta Jalili, Windsor (CA)

( * ) Notice: Subject to any disclaimer, the term of this patent is extended or adjusted under 35 U.S.C. 154(b) by 124 days.

(21) Appl. No.: 15/006,189

(22) Filed: Jan. 26, 2016

(65) Prior Publication Data

US 2016/0278351 A1   Sep. 29, 2016

Related U.S. Application Data

(63) Continuation of application No. 14/679,482, filed on Apr. 6, 2015, now Pat. No. 9,265,238, which is a continuation-in-part of application No. 13/987,769, filed on Aug. 30, 2013, now Pat. No. 9,185,890.

(60) Provisional application No. 61/695,719, filed on Aug. 31, 2012, provisional application No. 61/743,501, filed on Sep. 6, 2012.

(51) Int. Cl.
*A01K 67/027* (2006.01)
*A61K 49/00* (2006.01)

(52) U.S. Cl.
CPC ...... *A01K 67/0278* (2013.01); *A01K 67/0275* (2013.01); *A61K 49/0008* (2013.01); *A01K 2207/15* (2013.01); *A01K 2217/052* (2013.01); *A01K 2227/105* (2013.01); *A01K 2267/0331* (2013.01)

(58) Field of Classification Search
CPC ................ A01K 67/0275; A01K 67/0278
See application file for complete search history.

(56) References Cited

U.S. PATENT DOCUMENTS

| 4,736,866 A | 4/1988 | Leder et al. |
| 5,925,803 A | 7/1999 | Leder et al. |

OTHER PUBLICATIONS

Blakely, Collin, M. et al., "Developmental stage determines the effects of MYC in the mammary epithelium", Development, 132 (2005): 1147-1160, The Company of Biologists.
Kirou, Evangelia, "Elucidating the Role of Spy1A during c-Myc Induced Mammary Tumor Development" (2011). Electronic Theses and Dissertations. Paper 290. Windsor, Canada.

*Primary Examiner* — Scott Long

(57) ABSTRACT

In one aspect, the invention provides a transgenic non-human animal model having germ cells and somatic cells containing an endogenous MMTV-SV40-Spy1A gene sequence introduced into said animal model or an ancestor of said animal model at an embryonic stage, wherein said gene sequence comprises a mouse mammary tumor virus gene (MMTV), a functionally disrupted SV40 gene (SV40) and a human Spy1A gene. In another aspect, the present invention provides a transgenic non-human animal model whose germ cells and somatic cells contain an endogenous Spy1A-pTRE-Tight gene sequence introduced into said animal model or an ancestor of said animal model at an embryonic stage. Preferably, the Spy1A-pTRE-Tight animal model expresses the Spy1A gene and develop cancer, preferably breast cancer, when administered with tetracycline, preferably doxycycline.

6 Claims, 15 Drawing Sheets

MMTV-SV40-SPY1A AND SPY1A-PTRE TRANSGENIC MOUSE MODELS

RELATED APPLICATIONS

This application is a continuation application of earlier U.S. application Ser. No. 14/679,482 filed 6 Apr. 2015, which is a continuation-in-part application of U.S. application Ser. No. 13/987,769 filed 30 Aug. 2013, which claims the benefit of 35 U.S.C. 119(e) to U.S. Provisional Application Ser. No. 61/695,719 filed on 31 Aug. 2012 and U.S. Provisional Application Ser. No. 61/743,501 filed on 6 Sep. 2012.

SCOPE OF THE INVENTION

In one aspect, the present invention provides a transgenic non-human animal model which is selected to overexpress Spy1A under the control of a MMTV promoter causing the animal model to develop cancer, and preferably breast cancer. In another aspect, the present invention provides a transgenic non-human animal model selected to express Spy1A in one or more tissues thereof when an antibiotic is fed to the animal, and leading to the development of cancer, most preferably breast cancer. In another aspect, the present invention provides a transgenic non-human animal model, preferably a mammal and most preferably a mouse model, which includes a MMTV-SV40-Spy1A gene sequence (hereinafter referred interchangeably as "MMTV-SV40-Spy 1A", "MMTV-SV40-Spy1", "MMTV-Spy1A" and "MMTV-Spy1"). The animal model of the invention may permit uses in the identification of agents for inhibiting or treating cancer, or namely breast cancer.

BACKGROUND OF THE INVENTION

Amid all cancers known to afflict the Canadian population, breast cancer (BC) is documented as the second leading cause of cancer deaths among females. Current knowledge of the molecular signatures and biochemical pathways that govern BC initiation and progression is far from comprehensive and requires further expansion in order to identify putative biomarkers that undoubtedly predict the correct therapeutic course of action to take with each patient. Due to the heterogeneous nature of cell types which cooperate to form a functional post-natal mammary gland, the various clinical forms of BC that may arise are currently distinguished based on prognostic criteria such as histological phenotype, steroid and growth factor receptor status, and tumor ability to metastasize to neighbouring lymph nodes. In order to fully understand the various molecular mechanisms underpinning the evolution of mammary tumorigenesis, post-pubertal mammary gland development is often looked upon to highlight critical signaling pathways that possess the inherent capacity to mutate and/or become deregulated in BC. Once maturity is established, the adult virgin mammary organ retains the ability to cycle through four development stages: virgin, pregnancy, lactation, followed by involution and reversion to a virgin-like state. During early pregnancy-induced lobuloalveolar development, elevated expression of prolactin, placental lactogens, and progesterone results in escalated rates of luminal epithelial proliferation, and promotes functional differentiation of alveolar precursor cells into specialized structures proficient in milk release. Parturition-induced lactogenesis functions to nourish neonates through alveolar milk production and secretion of colostrums into enlarged luminal ducts. Neonate weaning initiates extensive luminal alveolar cell death (apoptosis) and epithelial remodelling during involution, a process lasting for several days to allow for reinstatement of the mammary gland to a virgin-like appearance.

SUMMARY OF THE INVENTION

It has been appreciated that at a cellular level Speedy (Spy1A) plays a role in the DNA damage response, functioning to enhance cell survival and promote cell proliferation in lieu of apoptosis. Spy1A is capable of promoting precocious development and tumorigenesis. Hence, determining how Spy1 A protein levels are regulated may reveal novel information regarding the dynamics of cell cycle control during normal and abnormal growth conditions. Furthermore, non-degradable forms of Spy 1 A do not trigger intrinsic cell cycle checkpoints but, rather, promote cell proliferation and oncogenic cell transformation demonstration that this mechanism may contribute to tumorigenesis.

Further, it has been appreciated that Spy1A is a novel cell cycle gene whose product binds to cyclin-dependent kinase-2 (CDK2) and activates its kinase activity to promote cell cycle progression through a cyclin independent mechanism and to promote cell movement into DNA synthesis. Spy1A is expressed naturally at high levels in the proliferating mammary gland, and aberrant overexpression of Spy1A results in precocious mammary development and eventually tumorigenesis in vivo.

Spy1A elevation in c-Myc overexpressing tumors can be maintained during primary tumor culture, the MMTV-Myc mouse model, well documented for its ability to form aggressive mammary adenocarcinomas, may be utilized to derive a previously uncharacterized tumor cell line engineered to overexpress c-Myc (henceforth referred to as F5A1-2).

Induction of the mammary oncogene c-Myc upregulates Spy1A and it is further demonstrated that Spy1A protein levels are elevated in mammary tissue and breast tumors derived from MMTV-Myc transgenic mice. Spy1A knockdown in F5A1-2 cell lines led to downregulation of cyclin-dependent kinas inhibitors (CKI) p21 and p27, a 23% reduction in proliferation rate, and a shift in cellular phenotype to a spindle-like/fibroblastic morphology. Together, findings support that Spy1A plays a functional role in mammary-related c-Myc signal transduction, and acts downstream of ERα, c-Myc, and the MAPK cascade to regulate proliferation, mammary development, and carcinogenesis.

One possible non-limiting object of the present invention is to provide a powerful tool for the study of cancer, namely breast cancer. Specifically, in one aspect the invention provides a transgenic non-human animal model whose somatic cells contain at least one copy of a MMTV-Spy1 transgene causing Spy1A overexpression under the control of the MMTV promoter, and causing this animal model to develop cancer, or more particularly breast cancer. The animal is preferably hemizygous for the transgene.

In another aspect, the present invention provides a transgenic non-human animal model whose somatic cells contain a MMTV-Spy1A transgene which causes the animal model to develop cancer, or preferably breast or liver cancer.

In yet another aspect, the present invention provides a transgenic non-human animal model comprising germ cells and somatic cells containing an exogenous MMTV-SV40-Spy1A gene sequence introduced into said animal model or an ancestor of said animal model at an embryonic stage, wherein said gene sequence comprises a mouse mammary tumor virus gene (MMTV), a functionally disrupted SV40 gene (SV40) and a human Spy1A gene. It has been appreciated that a portion of an SV40 gene when incorporated into a transgenic construct, or preferably the MMTV-SV40-Spy1A gene sequence increases expression or induce overexpression of a gene under the control of a MMTV promoter.

In a preferred embodiment, the transgenic non-human animal comprises germ cells and somatic cells containing an exogenous MMTV-SV40-Spy1A gene sequence introduced into said animal or an ancestor of said animal, at an embryonic stage wherein said gene sequences comprises a mouse mammary tumor virus promoter, a functionally disrupted SV40 gene and a human Spy1A gene.

Preferably, the animal model is hemizygous of the MMTV-SV40-Spy1A gene sequence. The human Spy1A gene preferably includes a modified Spy1A gene of SEQ ID NO: 1 or a conservatively modified variant thereof. Most preferably, the MMTV-SV40-Spy1A gene sequence is introduced to the animal model or the ancestor by microinjecting a fragment sequence obtained from restriction enzyme digestion of SEQ ID NO: 5 or a conservatively modified variant thereof with XhoI and SpeI.

In yet another aspect, the present invention provides a transgenic non-human animal model which is selected to express Spy1A in one or more tissues thereof when an antibiotic is fed to the animal model, said expression of Spy1A preferably leading to the development of cancer within said animal model, preferably breast or liver cancer.

In yet another aspect, the present invention provides a transgenic non-human animal model whose germ cells and somatic cells contain an exogenous Spy1A-pTRE-Tight gene sequence (hereinafter interchangeably referred to as "Flag-Spy1A-pTRE", "Flag-Spy1A-pTRE-Tight", "Flag-Spy1-pTRE", "Flag-Spy1-pTRE-Tight", "Spy 1A-pTRE", "Spy 1A-pTRE-Tight", "Spy1-pTRE" and "Spy1-pTRE-Tight") introduced into the animal model or an ancestor of the animal model at an embryonic stage, wherein said gene sequence comprises a human Spy1A gene.

Preferably, the animal model is hemizygous of the Spy1A-pTRE-Tight gene sequence. The human Spy1A gene is preferably a modified Spy1A gene of SEQ ID NO: 1 or a conservatively modified variant thereof. Most preferably, the Spy1A-pTRE-Tight gene sequence is introduced to the animal model or the ancestor by microinjecting a fragment sequence obtained from restriction enzyme digestion of SEQ ID NO: 18 or a conservatively modified variant thereof with XhoI and AlwNI.

In a preferred embodiment, the animal model is selected to express the Spy1A gene and develop cancer when administered with a tetracycline. Most preferably, the tetracycline is doxycycline. Preferably, the cancer is breast or liver cancer.

The animal model of the present invention is not strictly limited to those belonging to any specific genus or species, provided that the animal model preferably permits introduction of exogenous genetic sequences to be incorporated into the genome. The animal model is preferably a mouse, a rat, a monkey, a sheep, a dog, a rabbit, or a horse. Most preferably, the animal model is a mouse or a rat.

In yet another aspect, the present invention provides a method of producing the transgenic non-human animal, the method comprising microinjecting the fragment sequence into a fertilized embryo and transplanting said fertilized embryo into a surrogate animal.

In yet another aspect, the present invention provides a tumor cell line comprising a plurality of cells, wherein the cells are derived from the animal model or comprise the fragment sequence.

In yet another aspect, the present invention provides a method for screening an agent for treating or preventing cancer, the method comprising administering the agent into the animal model or the tumor cell line and detecting size reduction of a tumor caused by the cancer. Preferably, the cancer is breast or liver cancer.

In yet another aspect, the present invention provides a transgenic non-human animal model comprising germ cells and somatic cells having an endogenous MTB-Spy1A gene sequence, wherein the animal model is a progeny generated by crossing a MMTV-rtTA non-human animal model and the animal model having the Spy1A-pTRE-Tight gene sequence derived from the fragment sequence obtained from restriction enzyme digestion of SEQ ID NO: 18 or a conservatively modified variant thereof with XhoI and AlwNI, the progeny being selected to express the Spy1A gene when administered with a tetracycline.

In yet another aspect, the present invention provides a transgenic non-human animal model, the animal model being a progeny obtained from breeding first and second ancestors, wherein the first ancestor comprises respective germ cells and somatic cells having an ancestor gene sequence introduced into the genome of the first ancestor at an embryonic stage, the ancestor gene sequence comprising a promoter sequence and a tetracycline transactivator (tTA) or reverse tetracycline transactivator (rtTA) gene sequence, and the second ancestor comprises respective germ cells and somatic cells having a Spy1A-pTRE-Tight gene sequence introduced into the genome of the second ancestor at an embryonic stage, the Spy1A-pTRE-Tight gene sequence comprising a human Spy1A gene.

In yet another aspect, the present invention provides a transgenic non-human animal model comprising germ cells and somatic cells having a plurality of gene sequences introduced into the genome of said animal model or an ancestor of said animal model at an embryonic stage, wherein a first one of said gene sequences comprises a promoter sequence and a tetracycline transactivator (tTA) or reverse tetracycline transactivator (rtTA) gene sequence, and a second one of said gene sequences comprises a Spy1A-pTRE-Tight gene sequence, the Spy1A-pTRE-Tight gene sequence comprising a human Spy1A gene.

In a preferred embodiment, the first ancestor is female, and the second ancestor is male. In one embodiment, the animal model comprises germ cells and somatic cells having the ancestor gene sequence and the Spy1A-pTRE-Tight gene sequence. In a further preferred embodiment, the animal model is selected to express the Spy1A gene and develop cancer, or more preferably breast cancer, when administered with a tetracycline, or more preferably a doxycycline.

It is to be appreciated that the promoter sequence is not restricted to any particular promoter sequence. In one embodiment, the promoter sequence is selected to induce transcription of the tTA or rtTA gene sequence in a target organ. Non-limiting examples of the target organ include the brain, heart, skin, liver, stomach, intestine, breast, and reproductive organs. In one embodiment, the promoter sequence comprises a mouse mammary tumor virus (MMTV) gene, and the target organ is the breast. In one embodiment, the ancestor gene sequence or the first gene sequence comprises the rtTA gene sequence.

In one embodiment, the animal model or the second ancestor is hemizygous of the Spy1A-pTRE-Tight gene sequence, and the human Spy1A gene comprises a modified human Spy1A gene of SEQ ID NO: 1 or a conservatively modified variant thereof. In one embodiment, the Spy1A-pTRE-Tight gene sequence is introduced into the genome by microinjecting a fragment sequence obtained from restriction enzyme digestion of SEQ ID NO: 18 or a conservatively modified variant thereof with XhoI and A1wNI.

Preferably, the conservatively modified variants have at least 70%, 75%, 80%, 85%, 90%, 95% or 99% sequence identity to the specific referenced nucleotide or amino acid sequence. The conservatively modified variants may include point mutations, as well as deletions, substitutions, insertions, transitions, amplifications, inversions, transversions or others of one or more nucleotide bases or amino acid residues.

BRIEF DESCRIPTION OF THE DRAWINGS

Reference may now be had to the following detailed description, taken together with the accompanying drawings in which.

DETAILED DESCRIPTION OF THE INVENTION

Figure 1:
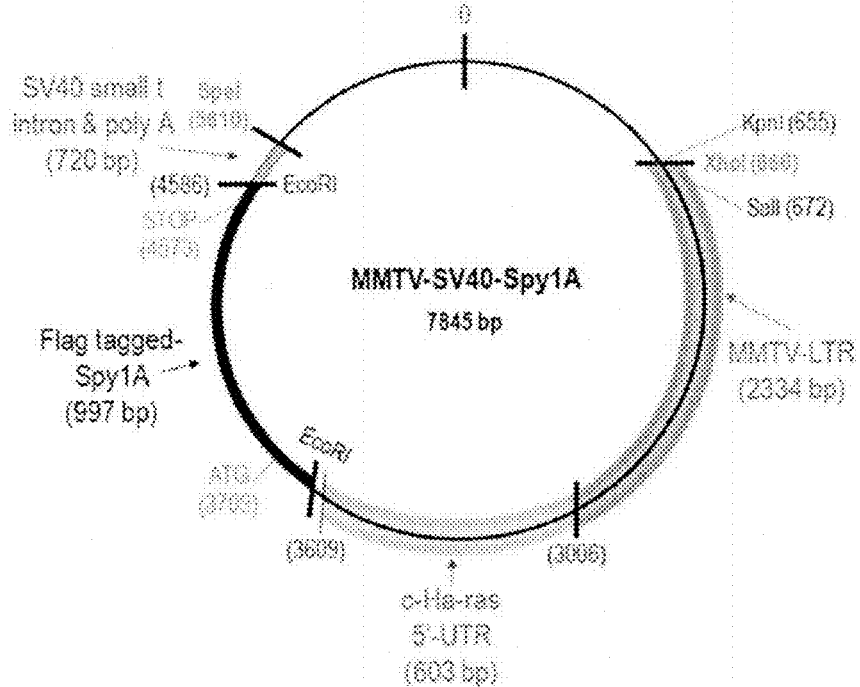
FIG. 1 shows a fusion gene fragment construct for producing a transgenic mouse according to an embodiment of the present invention.
Figure 2:
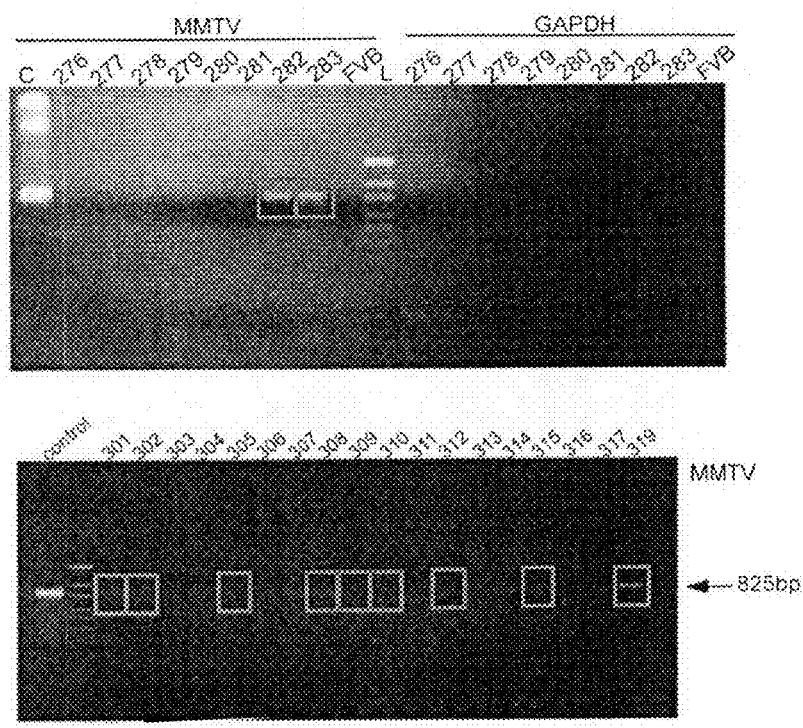
FIG. 2 shows identification of positive founders confirmed through PCR analysis. Positive founders are indicated by the presence of an 825 bp fragment.
Figure 3:
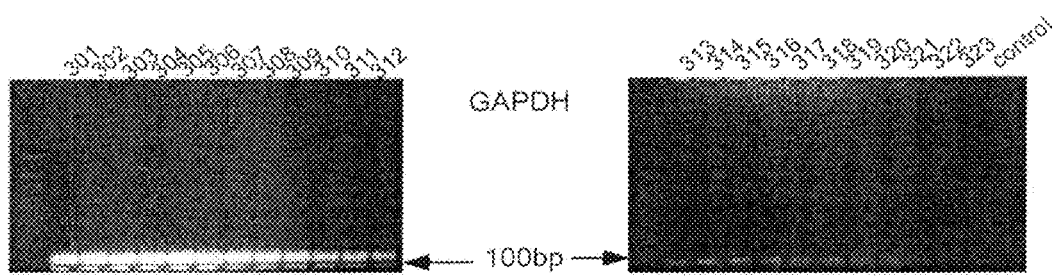
FIG. 3 shows GAPDH (100 bp) control for the identification of positive founders as shown in FIG. 2.

The gene fragment construct MMTV-SV40-Spy1A (SEQ ID NO: 5) for the development of a transgenic mouse according to a preferred embodiment of the present invention is shown in FIG. 1. The construct was micro injected at roughly 4.7 kb into 357 fertilized embryos from superovulated female mice and transplanted into pseudo pregnant CD-1 female mice. This resulted in 43 pups being born of which 13 tested positively for the MMTV-SV40-Spy1A as confirmed in the PCR analysis shown in FIGS. 2 and 3.

To prepare the MMTV-SV40-Spy1A construct, Flag-Spy1A-pLXSN containing the complete coding sequence of the human Spy1A gene conjugated to a flag tag was provided. Site-directed mutagenesis (SDM) was utilized to create a second EcoRI site positioned near the terminal region of the human Spy1A coding sequence (SEQ ID NO: 1) in Flag-Spy1A-pLXSN for efficient removal of the intrinsic poly-A tail.

GAATTCGCGGCCGCGTCGACCTGCGACGGAGCCTTGACCGCCGTTGCCCG

GCCCTCTCCCGCGCAGCCCCGGGCTTCCGCAGGAATATTGGGAAACCAAA

ATGAGGCACAATCAGATGTGTTGTGAGACACCACCTACTGTCACTGTTTA

TGTAAAATCAGGGTCAAATAGATCACATCAGCCTAAAAAGCCCATTACTC

TGAAGCGTCCTATTTGTAAAGATAATTGGCAAGCATTTGAAAAAAATACA

CATAATAACAACAAATCTAAACGCCCCAAAGGACCTTGTCTGGTTATACA

GCGTCAGGATATGACTGCTTTCTTTAAATTATTTGATGACGATTTAATTC

AAGATTTCTTGTGGATGGACTGCTGCTGTAAAATTGCAGACAAGTATCTT

TTGGCTATGACCTTTGTTTATTTCAAGAGGGCTAAATYTACTATAAGTGA

GCATACCAGGATAAATTTCTTTATTGCTCTGTATCTGGCTAATACAGTTG

AAGAAGATGAAGAAGAAACCAAGTACGAAATTTTTCCATGGGCTTTAGGG

AAAAACTGGAGAAAATTGTTCCCTAATTTCTTAAAGTTAAGGGACCAGCT

CTGGGATAGAATTGACTATAGGGCTATTGTAAGCAGGCGATGTTGTGAGG

AGGTTATGGCCATTGCACCAACCCATTATATCTGGCAAAGAGAACGTTCT

GTTCATCACAGTGGAGCTGTCAGAAACTACAACAGAGATGAAGTTCAGCT

GCCCCGGGGACCTAGTGCCACACCAGTAGATTGTTCACTCTGTGGTAAAA

AAAGAAGATATGTTAGACTGGGATTGTGTTCATCATCATCTTTATCCAGT

CATACAGCAGGGGTGACAGAAAAACATTCTCAGGACTCATACAACTCACT

GTCAATGGACATAATAGGTGATCCTTCTCAAGCTTATACTGGTTCTGAAG

GTATGATATAGTAATA

C  
                         ↑  
TGCCAGAATTAGATTTATGCATGTTGTTTACTGAGCTCTAGTCAGTCCTT

TCTGGCGGGATACATAATAATTTATATACTCCAACAATATGAGTTAAAT

TAATCTTGAAACTTTCTCCCCTTTCAGTTACTTTTTGTOTTGTGTCCATA

TTTGTTTTGTGGTGACCCACCTAAACAGATTTTTAATGTGACCTATGTTA

AGTTGAAAACTAATGCACCATAAGCCTCAGTATTTTAAGAGCCTGAATCA

TTTTTTTGAAATGTTTATTTTATTCAAAAGGGTTTCAAGAAGAAAATAAA

TTTACTTGTAATCTCAAAAAAAAAAAAAAAAAAAAAA

Figure 4:
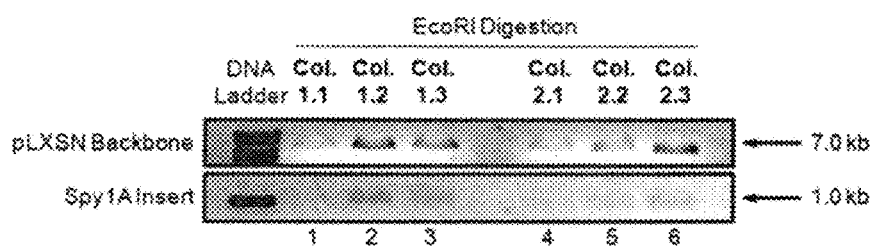
FIG. 4 shows identification of SDM-derived mutant Flag-Spy1A-pLXSN constructs upon detecting of a 977 bp fragment following EcoRI digestion of isolated plasmid DNA from each colony: colony 1.1 (lane 1); colony 1.2 (lane 2); colony 1.3 (lane 3); colony 2.1 (lane 4); colony 2.2 (lane 5); and colony 2.3 (lane 6). The pLXSN vector backbone was estimated at 7.0 kb, and the Spy1A insert was estimated at 1.0 kb (997 bp).

SDM primers A424 and A425 (SEQ ID NOs: 6 and 7) were designed to flank the vector region targeted for mutation. SDM reactions were performed with the following components: Flag-Spy1A-pLXSN vector DNA (10-100 ng); 0.3 mM dNTP mix (Cat. No. DD0057, Biobasic Inc., Ontario, Canada); 1× pfx buffer and 1 µl pfx polymerase (Cat. No. 11708-013, Invitrogen, Canada); 1mM MgSO4; 1 µM each of A424 forward and A425 reverse primers (SEQ ID NOs: 6 and 7); filter-sterilize nuclease free water up to 50.0 µl. Cycling conditions for SDM include (1) 2 minutes at 94° C., (2) 25 cycles of 94° C. for 15 seconds, 55° C. for 30 seconds and 68° C. for 5 seconds, and (3) 68° C. for 10 minutes. SDM reaction products were DpnI digested for 2 hours at 37° C. (Cat. No. ER1701, Fermentas, Burlington, Ontario, Canada), and subsequently transformed utilizing TOP10 E.coli and plated onto 100 mg/ml Ampicillin plates. Select colonies were screened for EcoRI insertion and were identified upon detection of a 977 bp fragment following EcoRI digestion (for 20 minutes at 37° C. (Cat. No. FD0274, Fermentas)) of isolated plasmid DNA from each colony (using QIAprep Spin Miniprep Kit (Cat. No. 27104, Qiagen, Mississauga, Ontario, Canada) as shown in FIG. 4. Successful EcoRI insertion was confirmed through sequencing for two colonies in particular, Is.1 and IIs.3, utilizing A210 and A211 sequencing primers (SEQ ID NOs: 8 and 9). Purified vector DNA from Colony IIs.3 was subjected to EcoRI digestion (Cat. No. ER0271, Fermentas), and produced two fragments at 7.0 kb (vector backbone) and 1.0 kb (Spy1A gene insert). Digestion products were separated, and the appropriate 1.0 kb fragment was gel extracted using the EZ-10 Spin Column DNA Gel Extraction Kit (Cat. No. BS354, Biobasic Inc.) and purified.

Figure 5:
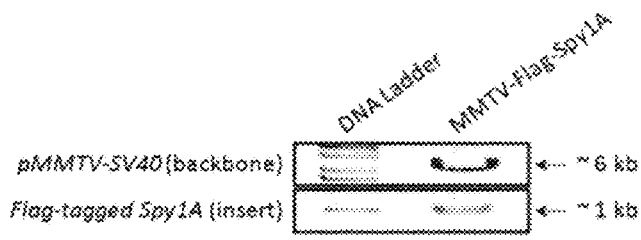
FIG. 5 shows EcoRI digestion of the MMTV-SV40-Spy1A transgenic vector releasing the flag-Spy1A coding sequence from the remaining vector backbone. EcoRI digestion of the resultant transgene DNC produced a 977 bp fragment as expected and confirmed successful cloning. The pMMTV-SV40 backbone was estimated at 6.0 kb and the flag-tagged Spy1A insert was estimated at 1.0 kb (997 bp).

EcoRI digestion of 2 mg of MMTV-SV40-TRPS-1 vector DNA ensued for 1 hour at 37°, followed by the immediate removal of terminal phosphate groups from digested ends utilizing incubation with calf intestinal alkaline phosphatase (Cat. No. EF0341, Fermentas) for 30 minutes at 37°. Phosphatase treatment was necessary in order to prevent the re-ligation of linearized vector DNA termini. Consequently, reaction products were separated, followed by gel purification of the resultant 6.0 kb fragment (MMTV-SV40 backbone) using the EZ-10 Spin Column DNA Gel Extraction Kit. Ligation of the Spy1A gene insert into the MMTV-SV40 backbone was conducted using T4 DNA ligase (Cat. No. EL0017, Fermentas), and ligation reactions were subsequently transformed utilizing TOP 10 E. coli and plated onto 100 mg/ml Ampicillin plates. Select colonies were screened for EcoRI insertion and were identified upon detection of a 977 bp fragment following EcoRI digestion of isolated plasmid DNA from each colony as shown in FIG. 5. Successful cloning of the Spy1A coding sequence into the MMTV-SV40 vector backbone was confirmed through sequencing. Sequencing primers A252, A253, A254, A255, A256, A257, A258 and A259 (SEQ ID NOs: 10 to 16) were utilized in order to verify the intactness of all transgenic vector components.

Figure 6:
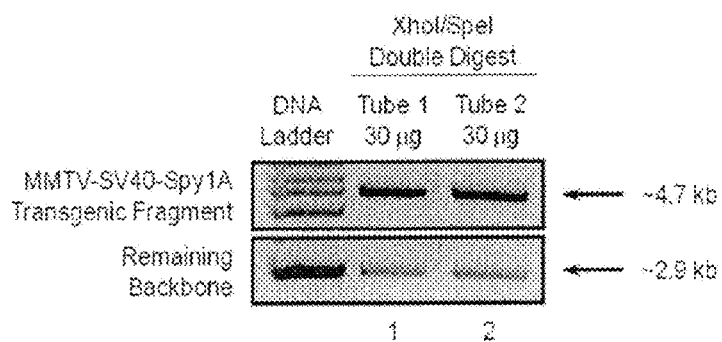
FIG. 6 shows digestion of MMTV-SV40-Spy1A prior to microinjection.
Figure 7:
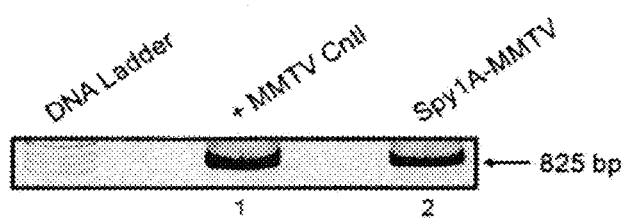
FIG. 7 shows detection of a single copy of MMTV-SV40-Spy1A DNA utilizing PCR genotyping methods. Transgene DNA was successfully detected using 8% PAGE in order to verify the success of using the MO23/MO23 primer set for detection of the Spy1A transgene in tail clip samples. PCR amplification of MMTV-SV40-Spy1A vector DNA (lane 2) using M022/M023 primers produced an 825 bp amplicon, identical to the positive MMTV vector control (+MMTV, lane 1) as expected.

The resultant transgenic vector was designated as MMTV-SV40-Spy1A and contains an untranslated portion of the Ha-ras gene, in addition to an SV40 polyadenylation site. Bacterial sequences such as those found in vector backbones have been noted to inhibit successful incorporation of transgenic DNA into the mouse blastocyst genome. Thus, XhoI/SpeI double digestion (Cat. Nos. ER0691 and ER1251, Fermentas) of purified vector DNA (30 mg per tube) ensued, and resulted in the production of two fragments: 4.7 kb (MMTV-SV40-Spy1A transgene) and 2.9 kb (remaining backbone) as shown in FIG. 6. Two vials of XhoI/SpeI digested transgenic DNA were made available for microinjection into mouse blastocysts for subsequent creation of the first MMTV-SV40-Spy1A transgenic mouse model known to date. Transgene detection of a single copy of MMTV-SV40-Spy1A DNA was tested utilizing the PCR conditions outlined for M022 and M023 genotyping primers (SEQ ID NOs: 2 and 4) as shown in FIG. 7.

Figure 8:
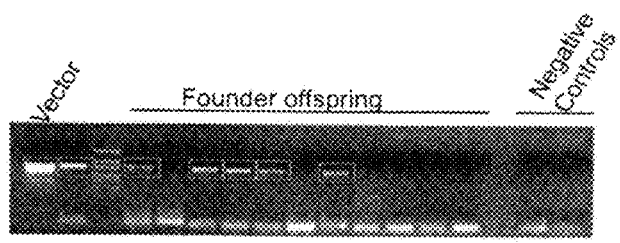
FIG. 8 shows successful transmission of transgene from founder to offspring using primer pair M022 (SEQ ID NO: 2)/M023 (SEQ ID NO: 4) resulting in a 825 bp fragment.
Figure 9:
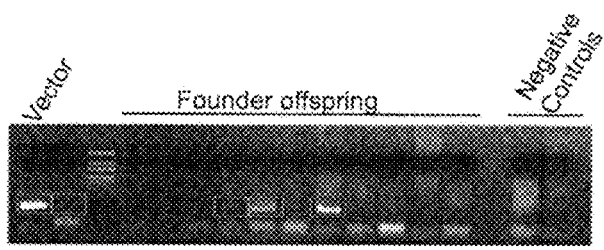
FIG. 9 shows confirmation of germline transmission of transgene using primer pair A933 (SEQ ID NO: 3)/M023 (SEQ ID NO: 4) resulting in 197 bp fragment.

The resulting transgene fragment was sent to the University of Western Ontario Transgenic Facility to undergo pronuclear injections. Tail samples from the resulting litters were received and DNA was extracted using the Qiagen Puregene Core Kit A for mouse tails. Transgene detection was accomplished using two sets of primers with two unique forward primers (M022 (SEQ ID NO: 2) and A933 (SEQ ID NO: 3)) and one reverse primer (M023 (SEQ ID NO: 4)). PCR cycling conditions consisted of (1) denaturation at 94° C. for 3 min, (2) denaturation at 94° C. for 1 min, annealing at 55° C. for 2 min, elongation at 72° C. for 1 min and (3) a final elongation step at 72° C. for 3 min. Each 25 uL PCR reaction was made using UBI HP Taq DNA polymerase (HPTAQ-01) and contained a final concentration of 2 ng/uL of pure genomic DNA, 1× buffer, 2 mM MgSO$_4$, 0.2 mM dNTP, 0.5 mM forward primer, 0.5 mM reverse primer and 0.025 U/uL Taq polymerase. Additionally, a final volume of 1% and 4% DMSO was added for primer pairs M022 (SEQ ID NO: 2)/M023 (SEQ ID NO: 4) and A933 (SEQ ID NO: 3)/M023 (SEQ ID NO: 4) respectively. PCR amplification resulted in an 825 bp and 197 bp amplicon for primers M022 (SEQ ID NO: 2)/M023 (SEQ ID NO: 4) and A933 (SEQ ID NO: 3)/M023 (SEQ ID NO: 4) respectively as shown in FIGS. 8 and 9, respectively.

Figure 23:
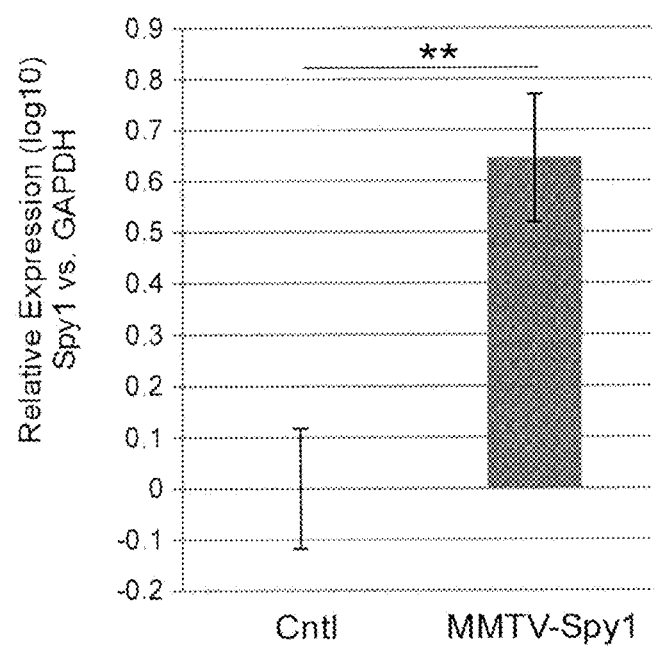
FIG. 23 shows a bar graph illustrating the results from a qRT PCR analysis test for Spy1 overexpression in the mammary glands of a MMTV-Spy1 mouse in accordance with a preferred embodiment of the invention, and which shows log 10 expression of Spy1 as the Y axis compared to GAPDH.
Figure 24:
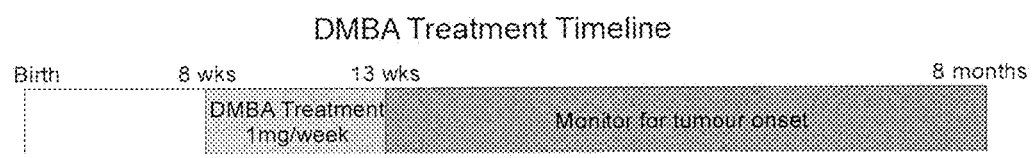
FIG. 24 shows a DMBA treatment plan for a MMTV-Spy1 mouse and its pair matched littermates, and which indicates age at beginning and end treatment.
Figure 25:
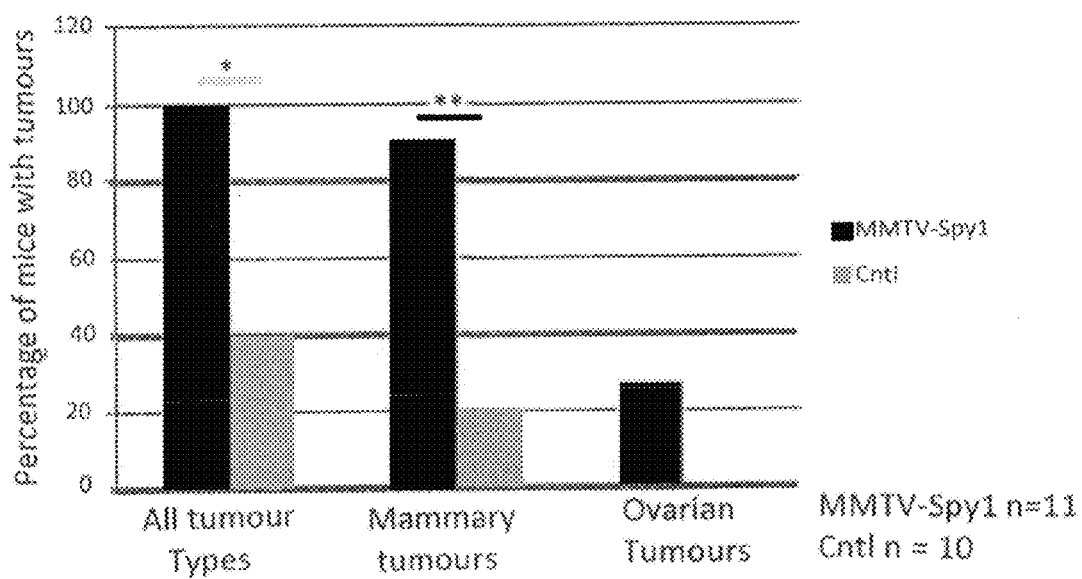
FIG. 25 shows a bar graph depicting the percentage of MMTV-Spy1 and control mice (Y axis) that developed all tumour types, mammary tumours, and ovarian tumours.
Figure 26:
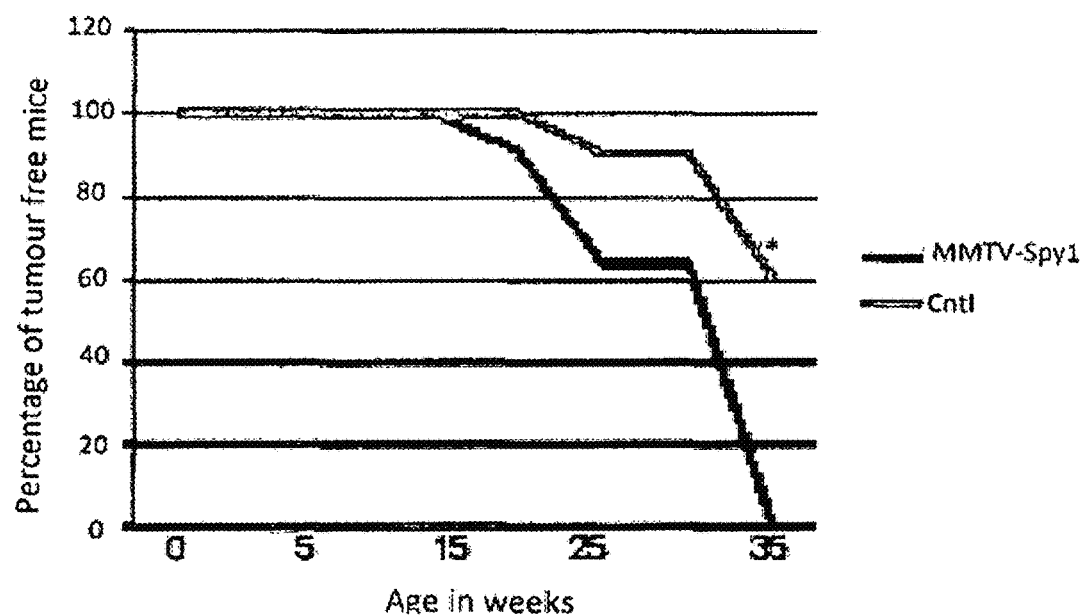
FIG. 26 shows a line graph depicting the percentage of tumour free mice (Y axis) at the indicated ages in weeks (X axis).

Expression levels of Spy1A was tested in the inguinal mammary glands of 6 week old MMTV-Spy1A mice and their negative littermates via qRT PCR analysis to ensure Spy1A was being overexpressed in the mammary gland of this mouse model system. Spy1A was found to be significantly overexpressed in the mammary glands of MMTV-Spy1A mice as compared to their control littermates (FIG. 23). To test for increased susceptibility to mammary tumourigenesis, MMTV-Spy 1 A mice and their negative littermates were treated with 1 mg of 7,12-dimethylbenzanthracene (DMBA) once a week for 6 consecutive weeks beginning at 8 weeks of age via oral gavage. Treatment plan indicating age during treatment and at end of study is illustrated in FIG. 24. Mice were monitored on a weekly basis for the development of mammary tumours via palpitation. MMTV-Spy1 A mice were found to develop significantly more mammary tumours than their control littermates (FIG. 25). Additionally, MMTV-Spy1A mice developed tumours earlier than their control littermates (FIG. 26).

Figure 27:
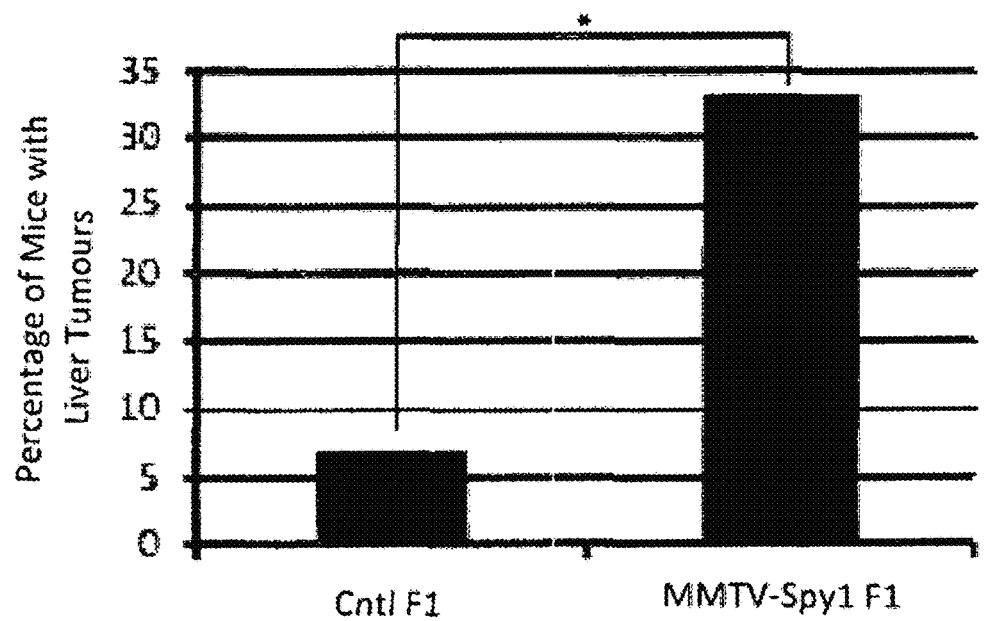
FIG. 27 shows a bar graph depicting the percentage of MMTV-Spy1 and pair matched littermates (F1 cntl) developing hepatocellular carcinoma 1 year of age and older.
Figure 28:
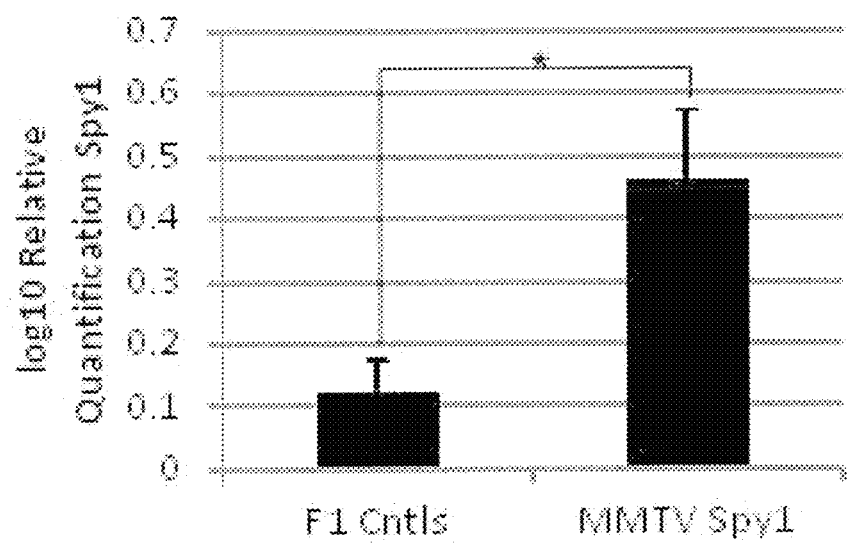
FIG. 28 shows a bar graph illustrating the results from a qRT PCR conducted on liver tissue collected from MMTV-Spy1 mice and their pair matched littermates, and which illustrates Spy1 expression on a log10 scale as compared to GAPDH.

When collecting male MMTV-Spy1 mice over the age of 1 year, it was noted there was an increased incidence of liver carcinogenesis in the MMTV-Spy1 mice as compared to their negative control littermates (FIG. 27). Liver tissue was collected from MMTV-Spy1 male mice 1 year of age and older along with pair matched littermate controls and the liver tissue was subjected to qRT PCR analysis to determine Spy1 expression in the liver. Spy1 was found to be significantly overexpressed in MMTV-Spy1 male mice as compared to littermate controls (FIG. 28).

Figure 10:
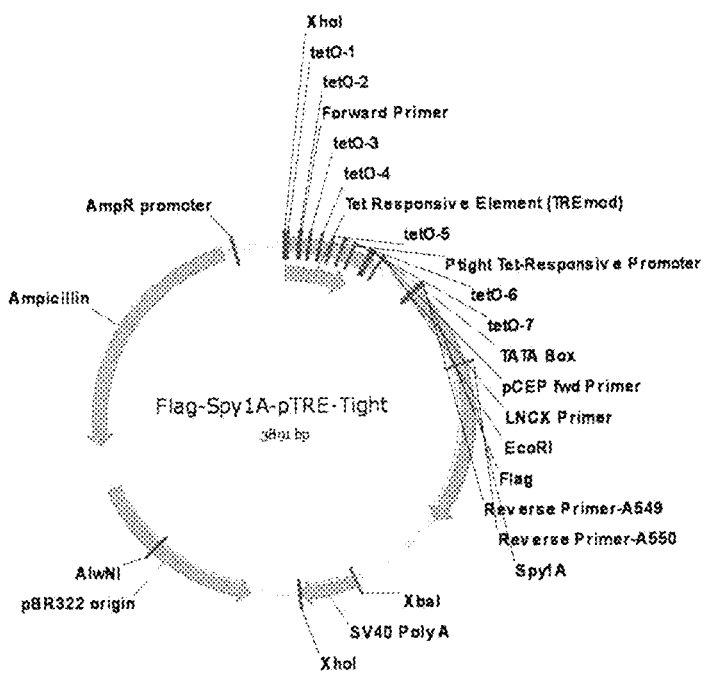
FIG. 10 shows a Spy1-pTRE vector map according to an embodiment of the present invention.
Figure 14:
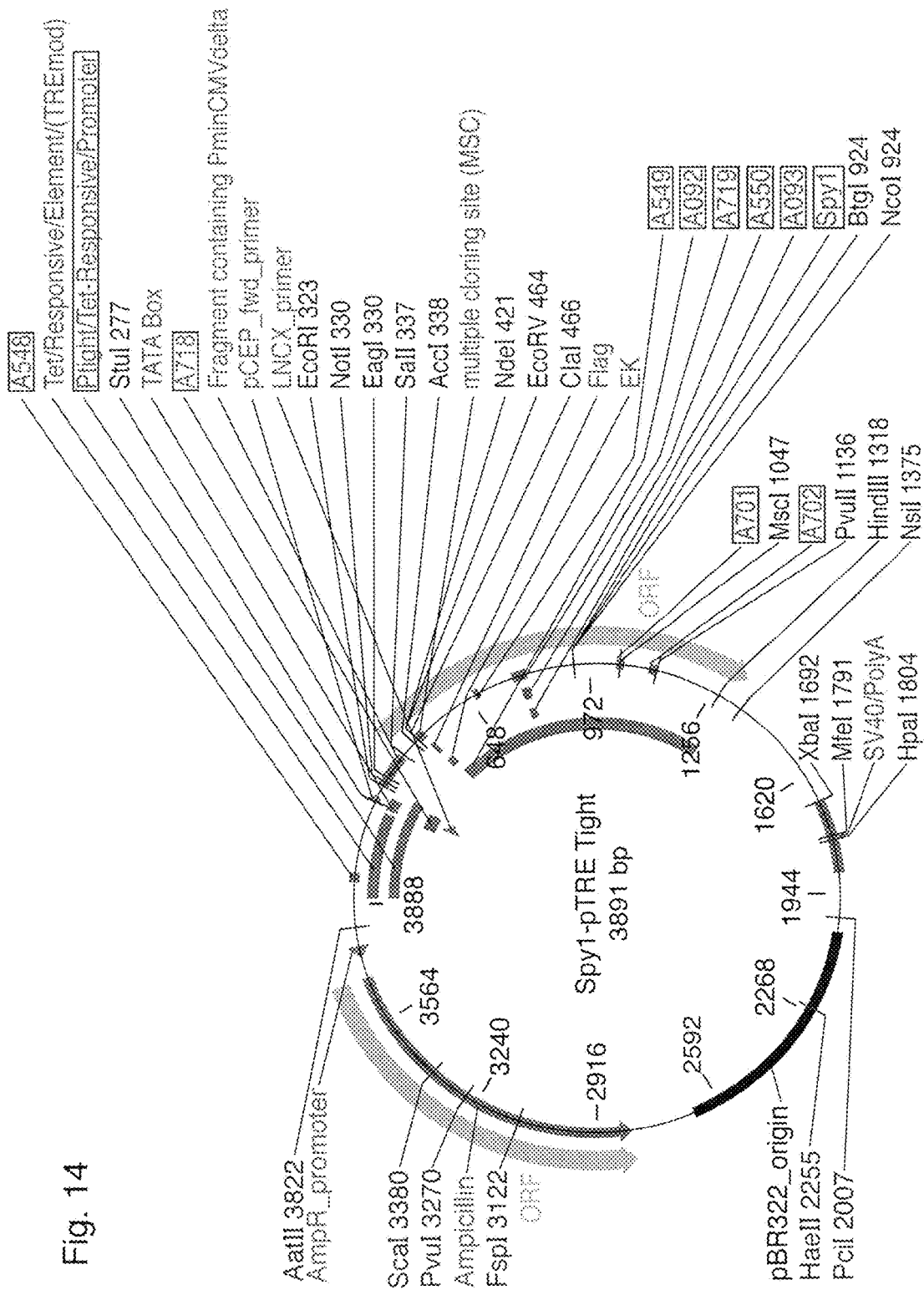
FIG. 14 shows a Flag-Spy1A-pTRE Tight vector map according to an embodiment of the present invention. Primers, Spy1 and pTRE promoter are outlined.
Figure 15:
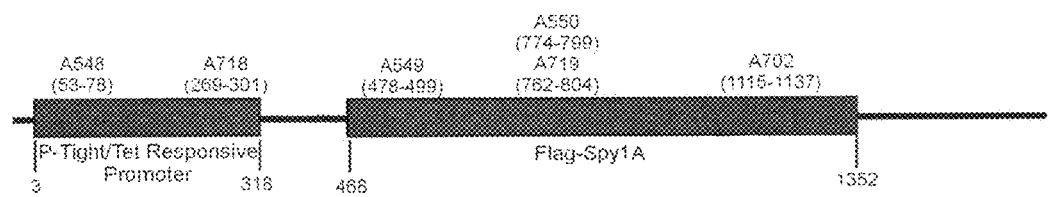
FIG. 15 shows a linearized map of a Flag-Spy1A-pTRE Tight vector indicating the locations of promoter, Spy1 and primers.
Figure 16:
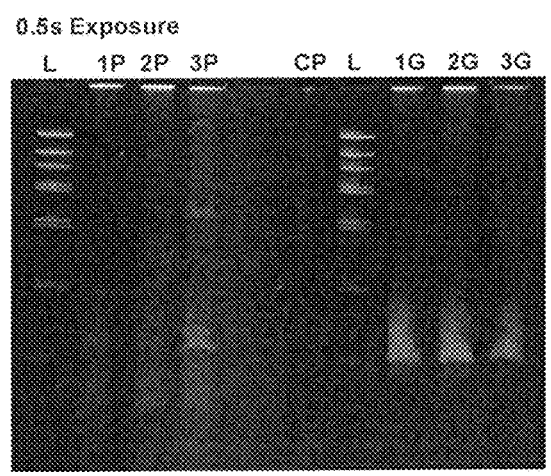
FIG. 16 shows a 4.25% polyacrylamide gel image of Spy1-pTRE DNA samples 1, 2 and 3 amplified with PCR using the primer combination A548/A549 with 0.5 second exposure time. The lane "L" corresponds to a ladder; the lanes 1P, 2P and 3P correspond to samples 1, 2 and 3, respectively; the lane "CP" corresponds to pTRE vector control (447 bp); and the lanes "G" correspond to GAPDH (about 100 bp).
Figure 17:
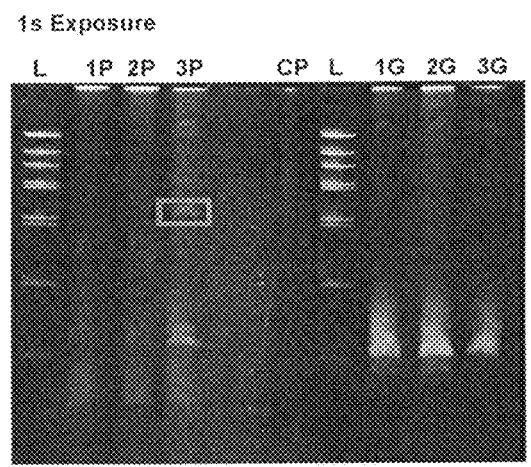
FIG. 17 shows a 4.25% polyacrylamide gel image of Spy1-pTRE DNA samples 1, 2 and 3 amplified with PCR using the primer combination A548/A549 with 1 second exposure time. The lane "L" corresponds to a ladder; the lanes 1P, 2P and 3P correspond to samples 1, 2 and 3, respectively; the lane "CP" corresponds to pTRE vector control (447 bp); and the lanes "G" correspond to GAPDH (about 100 bp). The band of correct size is outlined under the lane "3P".
Figure 18:
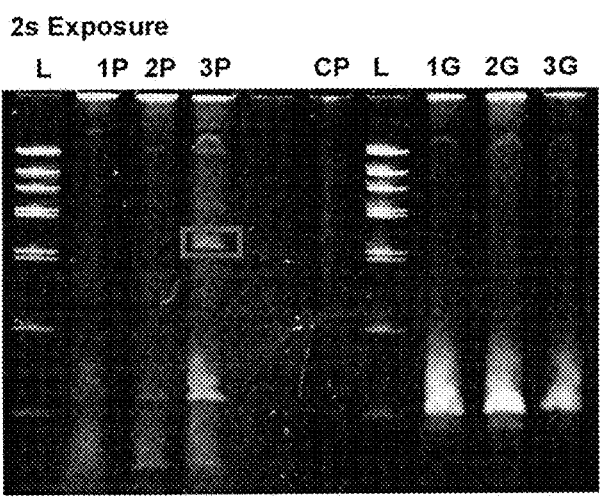
FIG. 18 shows a 4.25% polyacrylamide gel image of Spy1-pTRE DNA samples 1, 2 and 3 amplified with PCR using the primer combination A548/A549 with 2 second exposure time. The lane "L" corresponds to a ladder; the lanes 1P, 2P and 3P correspond to samples 1, 2 and 3, respectively; the lane "CP" corresponds to pTRE vector control (447 bp); and the lanes "G" correspond to GAPDH (about 100 bp). The band of correct size is outlined under the lane "3P".
Figure 19:
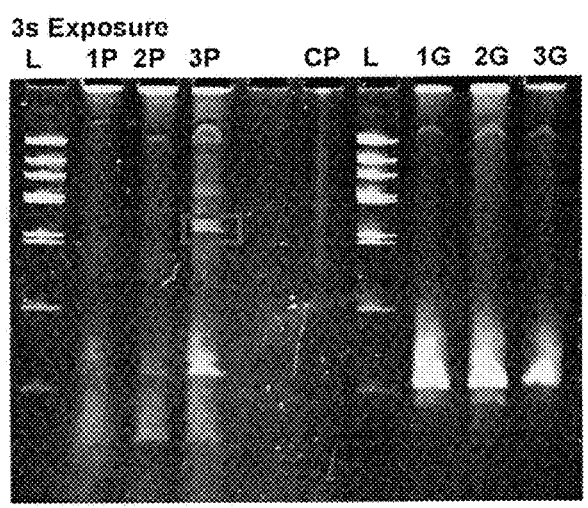
FIG. 19 shows a 4.25% polyacrylamide gel image of Spy1-pTRE DNA samples 1, 2 and 3 amplified with PCR using the primer combination A548/A549 with 3 second exposure time. The lane "L" corresponds to a ladder; the lanes 1P, 2P and 3P correspond to samples 1, 2 and 3, respectively; the lane "CP" corresponds to pTRE vector control (447 bp); and the lanes "G" correspond to GAPDH (about 100 bp). The band of correct size is outlined under the lane "3P".
Figure 20:
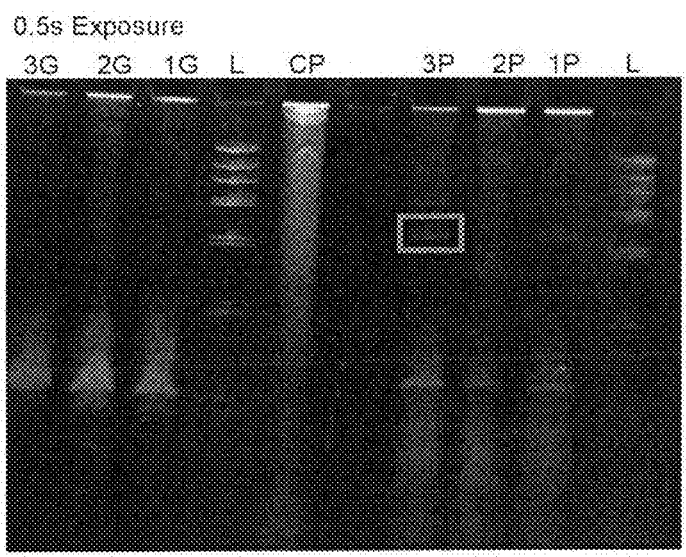
FIG. 20 shows a 4.25% polyacrylamide gel image of Spy1-pTRE DNA samples 1, 2 and 3 amplified with PCR using the primer combination A548/A549 with 0.5 second exposure time. The lane "L" corresponds to a ladder; the lanes 1P, 2P and 3P correspond to samples 1, 2 and 3, respectively; the lane "CP" corresponds to a maxi-prepped pTRE vector control with a higher concentration; and the lanes "G" correspond to GAPDH. The band of correct size is outlined under the lane "3P".
Figure 21:
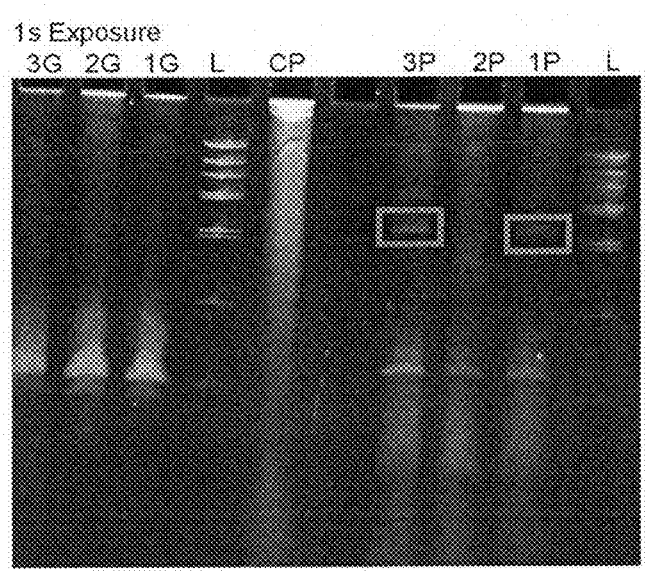
FIG. 21 shows a 4.25% polyacrylamide gel image of Spy1-pTRE DNA samples 1, 2 and 3 amplified with PCR using the primer combination A548/A549 with 1 second exposure time. The lane "L" corresponds to a ladder; the lanes 1P, 2P and 3P correspond to samples 1, 2 and 3, respectively; the lane "CP" corresponds to a maxi-prepped pTRE vector control with a higher concentration; and the lanes "G" correspond to GAPDH. The band of correct size is outlined under the lanes "1P" and "3P".
Figure 22:
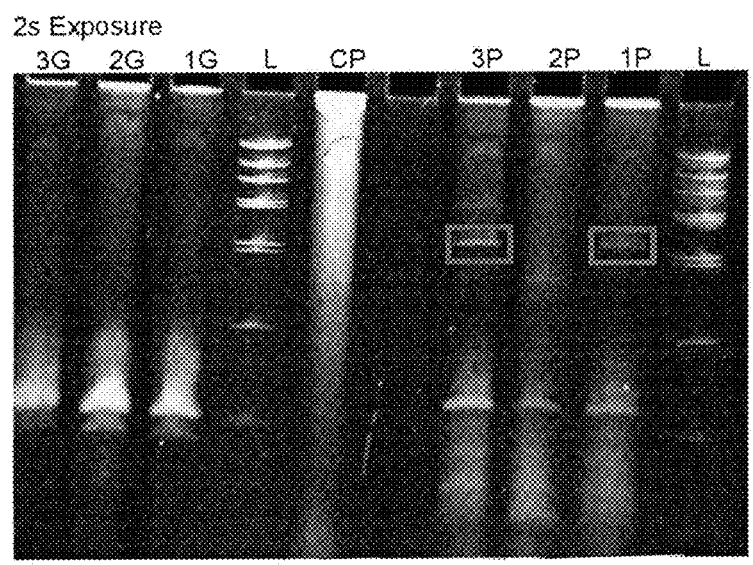
FIG. 22 shows a 4.25% polyacrylamide gel image of Spy1-pTRE DNA samples 1, 2 and 3 amplified with PCR using the primer combination A548/A549 with 2 second exposure time. The lane "L" corresponds to a ladder; the lanes 1P, 2P and 3P correspond to samples 1, 2 and 3, respectively; the lane "CP" corresponds to a maxi-prepped pTRE vector control with a higher concentration; and the lanes "G" correspond to GAPDH. The band of correct size is outlined under the lanes "1P" and "3P".

In accordance with another preferred embodiment of the present invention, the fusion gene fragment construct Flag-Spy1A-pTRE-Tight (SEQ ID NO: 18) as illustrated in FIGS. 10, 14 and 15 were prepared. In particular, a Caspase3-pTRE-Tight vector was digested with EcoRI and PvuII to remove Caspase3. A 20 bp linker was then added to close the vector. Site directed mutagenesis was performed on a Flag- Spy1A-pLXSN vector to create an EcoRI restriction enzyme site to enable extraction of Flag-Spy1A from the vector. EcoRI digestion was subsequently performed to remove Flag-Spy1A from the Flag-Spy1A-pLXSN vector. The Flag-Spy1A fragment was then ligated into the pTRE-Tight vector.

Successful preparation of DNA fusion gene fragment construct samples were confirmed by PCR amplification with the primer combination A548/A549 (SEQ ID NOs: 19 and 20) and polyacrylamide gel (as shown in FIGS. 16 to 22) as well as DNA sequencing. The bands of correct size are outlined under the lanes "1P" and/or "3P" in FIGS. 17 to 22. All tested PCR samples were confirmed by DNA sequencing.

Figure 11:
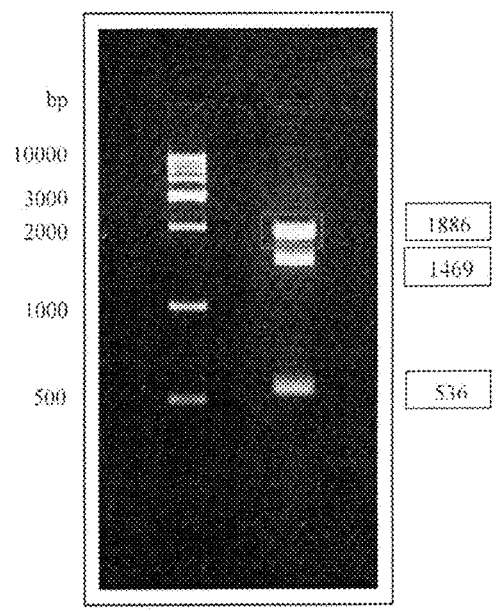
FIG. 11 shows a restriction digest of XhoI and A1wNI for isolating a portion of the vector illustrated FIG. 10 for a subsequent microinjection step according to an embodiment of the present invention.
Figure 12:
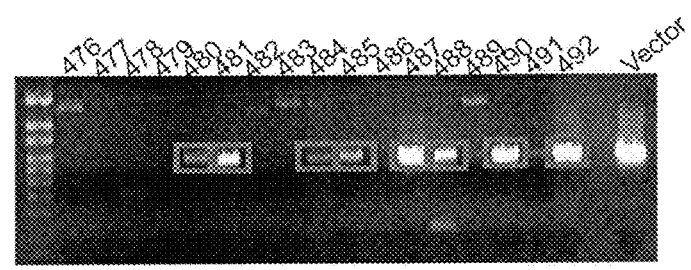
FIG. 12 shows identification of Spy1-pTRE founder mice via PCR analysis in the presence of a 536 bp band. The number labels correspond to mouse tag numbers belonging to each tail sample screened, and the label "vector" corresponds to the Spy1-pTRE transgenic vector used as a positive control.
Figure 13:
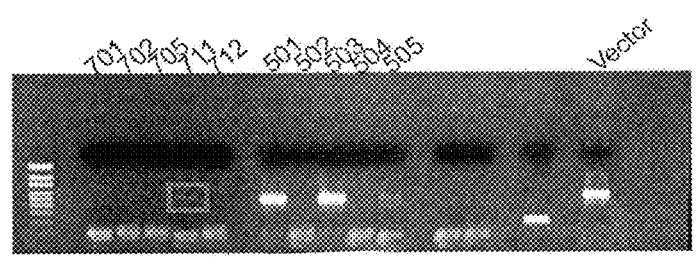
FIG. 13 shows confirmation of successful germline transmission of Spy1-pTRE transgene according to an embodiment of the present invention. The number labels correspond to mouse tag numbers belonging to each tail sample screened, and the label "vector" corresponds to the Spy1-pTRE transgenic vector used as a positive control.

The Spy1-pTRE plasmid were restriction digested using XhoI and A1wNI to isolate a portion for subsequent microinjection into a fertilized embryo from a superovulated female mouse. The digested portion was confirmed by gel electrophoresis as shown in FIG. 11. The digested portion was microinjected into fertilized embryos from superovulated female mice and transplanted into pseudo pregnant CD-1 female mice. Some resulting pups tested positive as confirmed and shown in FIG. 12. Successful germline transmission of the Spy1-pTRE transgene was confirmed as shown in FIG. 13.

The mice having the Spy1-pTRE gene sequence was fed doxycycline to activate expression of Spy1A. Development of cancer including breast cancer was experimentally confirmed.

Figure 29:
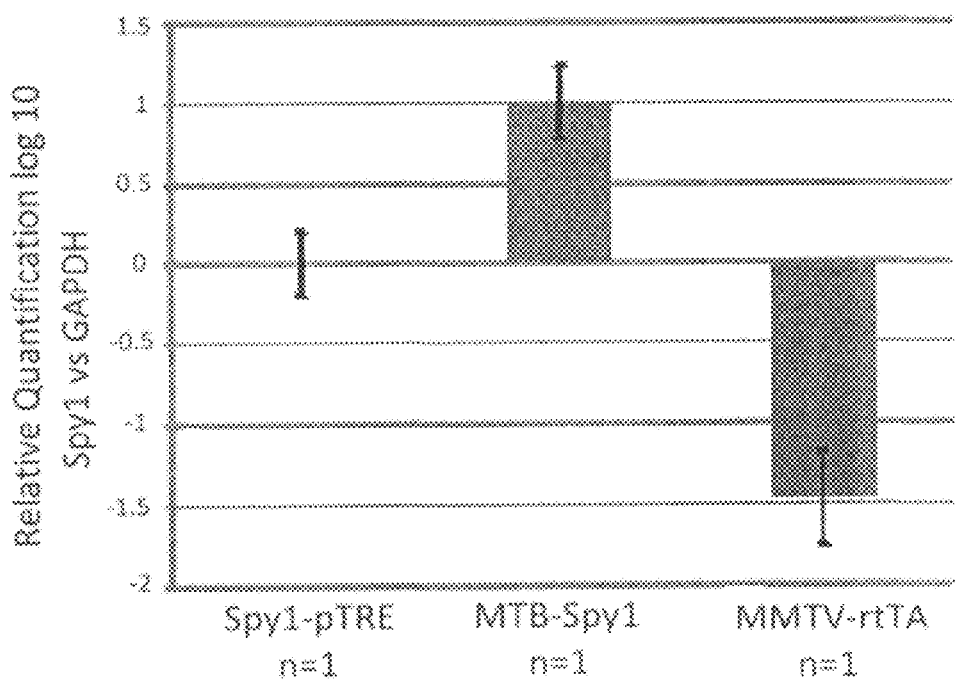
FIG. 29 shows a bar graph illustrating the results from a qRT PCR confirming Spy1 overexpression upon delivery of doxycycline to a MTB-Spy1 mouse generated by crossing a Spy1 -pTRE mouse with a MMTV-rtTA mouse.
Figure 30:
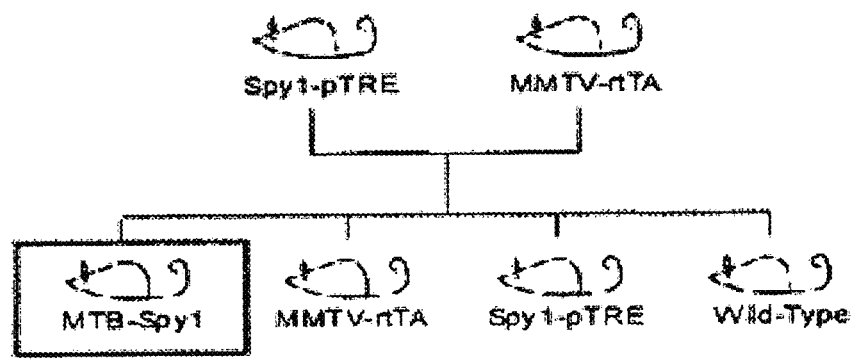
FIG. 30 shows a breeding scheme for a male Spy1-pTRE mouse in accordance with a preferred embodiment of the present invention and a female MMTV-rtTA mouse, and which illustrates possibly genotypes of the resulting progenies.

In a separate study, selected Spy1A-pTRE mice found to lack inducible overexpression of Spy1A were nevertheless found to be suitable for preparing overexpressing progenies. In a controlled study, selected Spy1-pTRE mice found to be without inducible overexpression of Spy1A were preferably crossed with MMTV-rtTA mice to generated a MTB-Spy1 mouse model. It has been appreciated that such animal model may permit inducible overexpression of Spy1 A preferably after administration of doxycycline to their diet in the form of food pellets. Indeed, expression of Spy1 was induced by administering 2 mg/mL of doxycycline at 5 weeks of age. Mammary glands were collected at 6 weeks of age from MTB-Spy1, Spy1-pTRE and MMTV-rtTA mice for qRT analysis to test for increased expression of Spy1 in the MTB-Spy1 mouse as compared to the selected control Spy1-pTRE and MMTV-rtTA mice. Spy1 was found to be overexpressed in the MTB-Spy1 mouse, indicating this model system is functioning correctly (FIG. 29).

Figure 31:
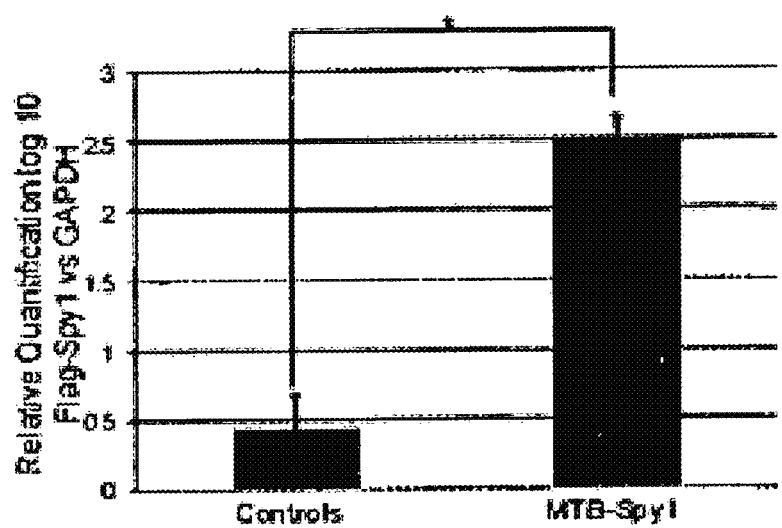
FIG. 31 shows a bar graph illustrating the results from a qRT PCR confirming elevated Spy1 expression upon delivery of doxycycline to a MTB-Spy1 progeny mouse generated by crossing a male Spy1 -pTRE parent mouse with a female MMTV-rtTA parent mouse.
Figure 32:
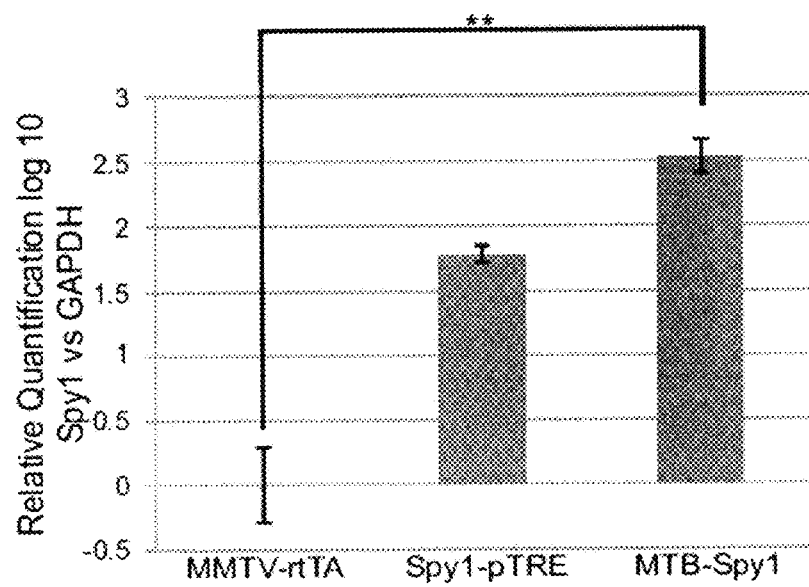
FIG. 32 shows a bar graph illustrating the results from a qRT PCR confirming elevated Spy1 expression upon delivery of doxycycline to a MTB-Spy1 progeny mouse generated by crossing a male Spy1-pTRE parent mouse with a female MMTV-rtTA parent mouse, when compared to the Spy1 expression of the parent mice.
Figure 33:
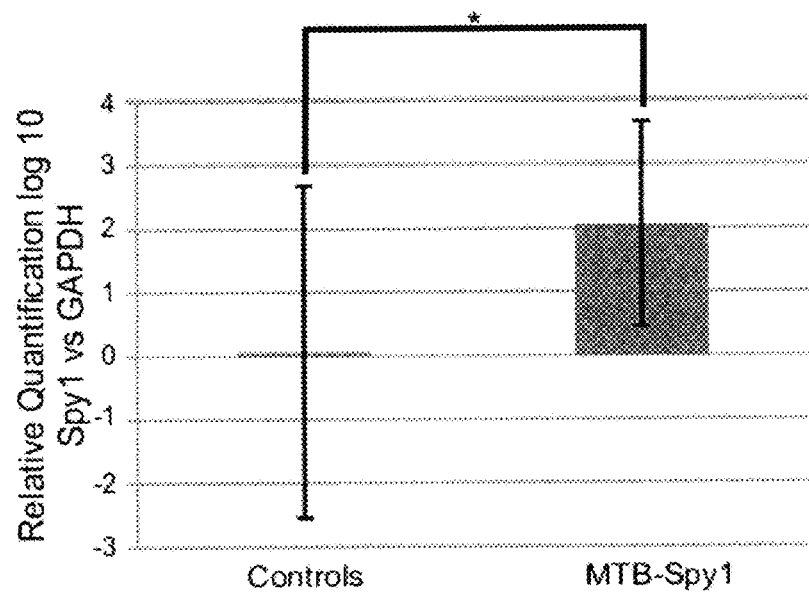
FIG. 33 shows a bar graph illustrating the results from a qRT PCR confirming elevated Spy1 expression in the mammary glands of a female MTB-Spy1 progeny mouse upon delivery of doxycycline thereto, and which is generated by crossing a male Spy1-pTRE parent mouse with a female MMTV-rtTA parent mouse.

In an additional study, a male Spy1-pTRE mouse in accordance with a preferred embodiment of the present invention was crossed with a female MMTV-rtTA mouse received from a collaborator, and which is described in Edward J. Funther et al. "A novel doxycycline-inducible system for the transgenic analysis of mammary gland biology". The FASEB Journal. 16.3 (2002): 283-292, the entire contents of which are hereby incorporated by reference. The female MMTV-rtTA mouse included the mouse mammary tumor virus gene (MMTV) and a reverse tetracycline transactivator (rtTA), such that the MMTV promotor portion drives the expression of rtTA ('Tet-On'). As illustrated in FIG. 29, four different genotypes were expected from the crossing, or namely a wild type progeny mouse, a Spy1-pTRE progeny mouse, an MMTV-rtTA progeny mouse and the intended MTB-Spy1 progeny mouse, the latter of which includes the transgenic elements from both parent mice. It has been appreciated that the intended MTB-Spy1 progeny mouse may permit for an inducible Tet-On system for expression of the Spy1 gene in the presence of a tetracycline, or preferably doxycycline, and as activated by the rtTA protein. As seen in FIGS. 31 to 33, qRT-PCR analysis confirmed that upon exposure to doxycycline, a MTB-Spy1 progeny female mouse showed elevated Spy1 expression in the mammary glands when compared to a control mouse, and the parent MMTV-rtTA and Spy1A-pTRE mice.

The applicant has appreciated that the present invention provides various advantages and applications, and which include without restriction a transgenic non-human animal model whose somatic cells contain at least one copy of a MMTV-Spy1A transgene causing the animal model to develop cancer.

In yet another aspect, the present invention provides a transgenic non-human animal model all of whose germ cells and somatic cells contain an exogenous MMTV-SV40-Spy1A gene sequence introduced into said mammal, or an ancestor of said mammal, at an embryonic stage wherein said gene sequence comprises a mouse mammary tumor virus gene (MMTV), a functionally disrupted SV40 gene (SV40) and a modified human Spy1A gene of SEQ ID NO: 1.

Other applications of the invention include without restriction:
  Methods of screening drugs/vaccines/or other vehicles developed for the prevention of the development of cancer;
  The study environmental factors and their effects on the development of cancer;
  The study cancer initiated at various stages of the animals development;
  Methods of screening drugs candidates and their anti-carcinogenic;
  Methods of screening drugs/vaccines/or other vehicles developed for the prevention of the development of cancer;
  The study environmental factors and their effects on the development of cancer; and
  The study of cancer namely breast cancer based on a novel expression of Spy1A initiated within a model animal by feeding the animal doxycycline.

Additional applications of the invention include, without restriction:
1. Expression of Spy1 A within one or more tissues of the model animal is activated by the animal model ingesting doxycycline (Dox).
2. The expression of Spy1A results in the tissues of the animal model results in the development of cancer namely breast cancer within that model animal.
3. A transgenic non-human animal model in this case being a mouse incorporates the condition and promoter response of claims 1 and 2.
4. The mouse animal model is able to pass this condition expressed in claims 1 and 2 along to subsequent generations when cross with a mouse not having this condition.
5. The transgenic non-human animal of claim 1, can be said animal selected from the group consisting of mice, rats, monkeys, sheep, and rabbits.
6. Analysis of animal model DNA is able to confirm that transgenic condition exists in said animal model.
7. Transgenic animal model may be used to:
  a. Study cancer
  b. Study cancer initiated at various stages of the animals development
  c. Method of screening drugs candidates and there anti-carcinogenic
  d. Method of screening drugs/vaccines/or other vehicles developed for the prevention of the development of cancer.
  e. Study environmental factors and their effects on the development of cancer.

We claim:

1. A method of producing a transgenic non-human animal model comprising germ cells and somatic cells having a Spy1A-pTRE-Tight gene sequence introduced into the genome of said animal model or an ancestor of said animal model at an embryonic stage, the gene sequence comprising a human Spy1A gene, wherein the method comprises microinjecting a fragment sequence obtained from restriction enzyme digestion of SEQ ID NO: 18 or a conservatively modified variant thereof with XhoI and AlwNI into a fertilized embryo and transplanting said fertilized embryo into a surrogate animal.

2. The method of claim 1, wherein said animal model is hemizygous of said Spy1A-pTRE-Tight gene sequence, and said human Spy1A gene comprises a modified human Spy1A gene of SEQ ID NO: 1 or a conservatively modified variant thereof.

3. The method of claim 1, wherein said animal is selected to express the Spy1A gene and develop cancer when administered with a tetracycline.

4. The method of claim 3, wherein said tetracycline is doxycycline.

5. The method of claim 3, wherein said cancer is breast cancer.

6. The method of claim 1, wherein said animal model is selected from the group consisting of a mouse and a rat.

* * * * *

SEQUENCE LISTING

<160> NUMBER OF SEQ ID NOS: 20

<210> SEQ ID NO 1
<211> LENGTH: 1303
<212> TYPE: DNA
<213> ORGANISM: Homo sapiens

<400> SEQUENCE: 1

| | | | | | |
|---|---|---|---|---|---|
| gaattcgcgg | ccgcgtcgac | ctgcgacgga | gccttgaccg | ccgttgcccg | gccctctccc | 60 |
| gcgcagcccc | gggcttccgc | aggaatattg | ggaaaccaaa | atgaggcaca | atcagatgtg | 120 |
| ttgtgagaca | ccacctactg | tcactgttta | tgtaaaatca | gggtcaaata | gatcacatca | 180 |
| gcctaaaaag | cccattactc | tgaagcgtcc | tatttgtaaa | gataattggc | aagcatttga | 240 |
| aaaaaataca | cataataaca | acaaatctaa | acgccccaaa | ggaccttgtc | tggttataca | 300 |
| gcgtcaggat | atgactgctt | tctttaaatt | atttgatgac | gatttaattc | aagatttctt | 360 |
| gtggatggac | tgctgctgta | aaattgcaga | caagtatctt | ttggctatga | cctttgttta | 420 |
| tttcaagagg | gctaaattta | ctataagtga | gcataccagg | ataaatttct | ttattgctct | 480 |
| gtatctggct | aatacagttg | aagaagatga | agaagaaacc | aagtacgaaa | tttttccatg | 540 |
| ggctttaggg | aaaaactgga | gaaaattgtt | ccctaatttc | ttaaagttaa | gggaccagct | 600 |
| ctgggataga | attgactata | ggctattgt | aagcaggcga | tgttgtgagg | aggttatggc | 660 |
| cattgcacca | acccattata | tctggcaaag | agaacgttct | gttcatcaca | gtggagctgt | 720 |
| cagaaactac | aacagagatg | aagttcagct | gccccgggga | cctagtgcca | caccagtaga | 780 |
| ttgttcactc | tgtggtaaaa | aagaagata | tgttagactg | ggattgtctt | catcatcatc | 840 |
| tttatccagt | catacagcag | gggtgacaga | aaaacattct | caggactcat | acaactcact | 900 |
| gtcaatggac | ataataggtg | atccttctca | agcttatact | ggttctgaag | gtatgatata | 960 |
| gtaatatgcc | agaattcgat | ttatgcatgt | tgtttactga | gctctagtca | gtcctttctg | 1020 |
| gcggggatac | ataataattt | atatactcca | acaatatgag | ttaaattaat | cttgaaactt | 1080 |
| tctcccctttt | cagttacttt | ttgtcttgtg | tccatatttg | ttttgtggtg | acccacctaa | 1140 |
| acagattttt | aatgtgacct | atgttaagtt | gaaaactaat | gcaccataag | cctcagtatt | 1200 |
| ttaagagcct | gaatcatttt | tttgaaatgt | ttattttatt | caaaagggtt | tcaagaagaa | 1260 |
| aataaattta | cttgtaatct | caaaaaaaaa | aaaaaaaaa | aaa | | 1303 |

<210> SEQ ID NO 2
<211> LENGTH: 24
<212> TYPE: DNA
<213> ORGANISM: Artificial Sequence
<220> FEATURE:
<223> OTHER INFORMATION: Forward primer 1 (M022)

<400> SEQUENCE: 2
cccaaggctt aagtaagttt ttgg                                         24

<210> SEQ ID NO 3
<211> LENGTH: 22
<212> TYPE: DNA
<213> ORGANISM: Artificial Sequence
<220> FEATURE:
<223> OTHER INFORMATION: Forward primer 3 (A933)

<400> SEQUENCE: 3
cccgctctag tggcagtgtg tt                                           22

-continued

```
<210> SEQ ID NO 4
<211> LENGTH: 24
<212> TYPE: DNA
<213> ORGANISM: Artificial Sequence
<220> FEATURE:
<223> OTHER INFORMATION: Reverse primer (M023)

<400> SEQUENCE: 4
gggcataagc acagataaaa cact                                          24

<210> SEQ ID NO 5
<211> LENGTH: 7911
<212> TYPE: DNA
<213> ORGANISM: Artificial Sequence
<220> FEATURE:
<223> OTHER INFORMATION: MMTV-SV40-Spy1A fusion gene fragment construct

<400> SEQUENCE: 5
cacctaaatt gtaagcgtta atattttgtt aaaattcgcg ttaaattttt gttaaatcag    60 ctcattttt aaccaatagg ccgaaatcgg caaaatccct tataaatcaa aagaatagac    120
cgagataggg ttgagtgttg ttccagtttg gaacaagagt ccactattaa agaacgtgga   180
ctccaacgtc aaagggcgaa aaaccgtcta tcagggcgat ggcccactac gtgaaccatc   240
accctaatca agttttttgg ggtcgaggtg ccgtaaagca ctaaatcgga accctaaagg   300
gagcccccga tttagagctt gacggggaaa gccggcgaac gtggcgagaa aggaagggaa   360
gaaagcgaaa ggagcgggcg ctagggcgct ggcaagtgta gcggtcacgc tgcgcgtaac   420
caccacaccc gccgcgctta atgcgccgct acagggcgcg tcccattcgc cattcaggct   480
gcgcaactgt tgggaagggc gatcggtgcg ggcctcttcg ctattacgcc agctggcgaa   540
agggggatgt gctgcaaggc gattaagttg ggtaacgcca gggttttccc agtcacgacg   600
ttgtaaaacg acggccagtg aattgtaata cgactcacta tagggcgaat gggtaccgg   660 gcccccctc gaggtcgacg ctctcccta tgcgactcct gcattaggaa gcagcccagt    720
agtaggttga ggccgttgag caccgccgcc gcaaggaatg gtgcatgcaa ggagatggcg   780
cccaacagtc ccccggccac ggggcctgcc accatacca gccgaaaca agcgctcatg   840 agcccgaagt ggcgagcccg atcttcccca tcggtgatgt cggcgatata ggcgccagca   900
accgcacctg tggcgccggt gatgccggcc acgatgcgtc cggcgtagag gatcccaatg   960
atagagattt tactgctcta gttccccata cagaattgtt tcgcttagtt gcagcctcaa   1020
gatatcttat tctcaaaagg ccaggatttc aagaacatga catgattcct acatctgcct   1080
gtgttactta cccttatgcc atattattag gattacctca gctaatagat atagagaaaa   1140
gaggatctac ttttcatatt tcctgttctt cttgtagatt gactaattgt ttagattctt   1200
ctgcctacga ctatgcagcg atcatagtca agaggccgcc atacgtgctg ctacctgtag   1260
atattggtga tgaaccatgg tttgatgatt ctgccattca aacctttagg tatgccacag   1320
atttaattcg agccaagcga ttcgtcgctg ccattattct gggcatatct gctttaattg   1380
ctattatcac ttcctttgct gtagctacta ctgctttagt taaggagatg caaactgcta   1440
cgtttgttaa taatcttcat aggaatgtta cattagccttt atctgaacaa agaataatag   1500
atttaaaatt agaagctaga cttaatgctt tagaagaagt agtttttagag ttgggacaag   1560 atgtggcaaa cttaaagacc agaatgtcca ccaggtgtca tgcaaattat gatttttatct   1620 gcgttacacc tttaccatat aatgcttctg agagctggga aagaaccaaa gctcatttat   1680
tgggcatttg gaatgacaat gagatttcat ataacataca agaattaacc aacctgatta   1740
```

```
gtgatatgag caaacaacat attgacacag tggacctcag tggcttggct cagtcctttg    1800
ccaatggagt aaaggcttta aatccattag attggacaca atatttcatt tttataggtg    1860
ttggagccct gcttttagtc atagtgctta tgattttccc cattgttttc cagtgccttg    1920
cgaagagcct tgaccaagtg cagtcagatc ttaacgtgct tcttttaaaa aagaaaaaag    1980
ggggaaatgc cgcgcctgca gcagaaatgg ttgaactccc gagagtgtcc tacacctagg    2040
ggagaagcag ccaaggggtt gtttcccacc aaggacgacc cgtctgcgca caaacggatg    2100
agcccatcag acaaagacat attcattctc tgctgcaaac ttggcatagc tctgctttgc    2160
ctggggctat tggggaagt tgcggttcgt gctcgcaggg ctctcaccct tgactctttt    2220
aatagctctt ctgtgcaaga ttacaatcta aacaattcgg agaactcgac cttcctcctg    2280
aggcaaggac cacagccaac ttcctcttac aagccgcatc gattttgtcc ttcagaaata    2340
gaaataagaa tgcttgctaa aaattatatt tttaccaata agaccaatcc aataggtaga    2400
ttattagtta ctatgttaag aaatgaatca ttatctttta gtactatttt tactcaaatt    2460
cagaagttag aaatgggaat agaaaataga aagagacgct caccctcaat tgaagaacag    2520
gtgcaaggac tattgaccac aggcctagaa gtaaaaaagg gaaaaaagag tgttttttgtc   2580 aaaataggag acaggtggtg gcaaccaggg acttataggg gaccttacat ctacagacca    2640
acagatgccc ccttaccata tacaggaaga tatgacttaa attgggatag gtgggttaca    2700
gtcaatggct ataaagtgtt atatagatcc ctccctttc gtgaaagact cgccagagct     2760
agacctcctt ggtgtatgtt gtctcaagaa gaaaagacg acatgaaaca acaggtacat    2820
gattatattt atctaggaac aggaatgcac ttttggggaa agattttcca taccaaggag    2880
gggacagtgg ctggactaat agaacattat tctgcaaaaa cttatggcat gagttattat    2940
gaatagcctt tattggccca accttgcggt tcccagggct taagtaagtt tttggttaca    3000
aactgttctt aaaacgagga tgtgagacaa gtggtttcct gacttggttt ggtatcaaag    3060
gttctgatct gagctctgag tgttctattt tcctatgttc ttttggaatt tatccaaatc    3120
ttatgtaaat gcttatgtaa accaagatat aaaagagtgc tgatttttg agtaaacttg     3180 caacagtcct aacattcacc tcttgtgtgt ttgtgtctgt tcgccatccc gtctccgctc    3240
gtcacttatc cttcactttc cagagggtcc ccccgcagac cccggcgtag aggatccgca    3300
cccttgatga ctccgtctga attttttggtt tcagtttggt accgaagctg cgcggcgcgt    3360
ctgcttgtta cttgtttgac tgttggaatt gtttgtcttc tttgtgacct gactgtggtt    3420
ttctggacgt gttgtgtctg ttagtgtctt tttgactttt gtttcgtgtt tgaatttgga    3480
ctgacgactg tgtttaaaat cttagaccga cgactgtgtt tgaaatcatg aaactgtttg    3540
ctttgttcgt cgaagagttt tacttggtcc ccttaacgct tagtgagtaa gaaacttaat    3600
tttgtagacc ccgctctagt ggcagtgtgt tggttgatag ccaaagttaa tttttaaaac    3660
atagtgtttt gggggttggg gatttagctc agtgatagag ctcttgccta gcaagcgcaa    3720
ggccctgggt tcggtcccca gctctgaaaa aaaggaaaga gaaacaaaac aaaaacatat    3780
agtgttttat ctgtgcttat gcccgcagcc cgagccgcac ccgccgcgga cggagcccat    3840
gcgcgggccc agtcggcgcc cgtccgcgcc ccgccctgc cccggccccg gcccccaagc     3900
ttgatatcga attcgcggcc gcgtcgacct gcgacggagc cttgaccgcc gttgcccggc    3960
cctctcccgc gcagccccgg gcttccgcag gaatattggg aaacccatat ggactacaaa    4020
gaccatgacg gtgattataa agatcatgat atcgattaca aggatgacga tgacaagagg    4080
cacaatcaga tgtgttgtga gacaccacct actgtcactg tttatgtaaa atcagggtca    4140
```

```
aatagatcac atcagcctaa aaagcccatt actctgaagc gtcctatttg taaagataat   4200
tggcaagcat ttgaaaaaaa tacacataat aacaacaaat ctaaacgccc caaaggacct   4260
tgtctggtta tacagcgtca ggatatgact gctttctta aattatttga tgacgattta    4320
attcaagatt tcttgtggat ggactgctgc tgtaaaattg cagacaagta tcttttggct   4380
atgacctttg tttatttcaa gagggctaaa tttactataa gtgagcatac caggataaat   4440
ttctttattg ctctgtatct ggctaataca gttgaagaag atgaagaaga aaccaagtac   4500
gaaatttttc catgggcttt agggaaaaac tggagaaaat tgttccctaa tttcttaaag   4560
ttaagggacc agctctggga tagaattgac tatagggcta ttgtaagcag gcgatgttgt   4620
gaggaggtta tggccattgc accaacccat tatatctggc aaagagaacg ttctgttcat   4680
cacagtggag ctgtcagaaa ctacaacaga gatgaagttc agctgccccg gggacctagt   4740
gccacaccag tagattgttc actctgtggt aaaaaaagaa gatatgttag actgggattg   4800
tcttcatcat catcttatc cagtcataca gcagggtga cagaaaaaca ttctcaggac     4860
tcatacaact cactgtcaat ggacataata ggtgatcctt ctcaagctta tactggttct   4920
gaaggtatga tatagtaata tgccagaatt cctgcaggtc gcggccgcga ctctagagga   4980
tctttgtgaa ggaaccttac ttctgtggtg tgacataatt ggacaaacta cctacagaga   5040
tttaaagctc taaggtaaat ataaaatttt taagtgtata atgtgttaaa ctactgattc   5100
taattgtttg tgtattttag attccaacct atggaactga tgaatgggag cagtggtgga   5160
atgcctttaa tgaggaaaac ctgttttgct cagaagaaat gccatctagt gatgatgagg   5220
ctactgctga ctctcaacat tctactcctc caaaaaagaa gagaaaggta gaagacccca   5280
aggactttcc ttcagaattg ctaagttttt tgagtcatgc tgtgtttagt aatagaactc   5340
ttgcttgctt tgctatttac accacaaagg aaaaagctgc actgctatac aagaaaatta   5400
tggaaaaata tttgatgtat agtgccttga ctagagatca taatcagcca taccacattt   5460
gtagaggttt tacttgcttt aaaaaacctc ccacacctcc cctgaacct gaaacataaa    5520 atgaatgcaa ttgttgttgt taacttgttt attgcagctt ataatggtta caaataaagc   5580
aatagcatca caaatttcac aaataaagca tttttttcac tgcattctag ttgtggtttg   5640
tccaaactca tcaatgtatc ttatcatgtc tggatccact agttctagag cggccgccac   5700
cgcggtggag ctccagcttt tgttcccttt agtgagggtt aatttcgagc ttggcgtaat   5760
catggtcata gctgtttcct gtgtgaaatt gttatccgct cacaattcca cacaacatac   5820
gagccggaag cataaagtgt aaagcctggg gtgcctaatg agtgagctaa ctcacattaa   5880
ttgcgttgcg ctcactgccc gctttccagt cgggaaacct gtcgtgccag ctgcattaat   5940
gaatcggcca acgcgcgggg agaggcggtt tgcgtattgg gcgctcttcc gcttcctcgc   6000
tcactgactc gctgcgctcg gtcgttcggc tgcggcgagc ggtatcagct cactcaaagg   6060
cggtaatacg gttatccaca gaatcagggg ataacgcagg aaagaacatg tgagcaaaag   6120
gccagcaaaa ggccaggaac cgtaaaaagg ccgcgttgct ggcgtttttc cataggctcc   6180
gcccccctga cgagcatcac aaaaatcgac gctcaagtca gaggtggcga aacccgacag   6240
gactataaag ataccaggcg tttccccctg gaagctccct cgtgcgctct cctgttccga   6300
cctgccgctt accggatac ctgtccgcct ttctcccttc gggaagcgtg gcgctttctc    6360
atagctcacg ctgtaggtat ctcagttcgg tgtaggtcgt tcgctccaag ctgggctgtg   6420
tgcacgaacc ccccgttcag cccgaccgct gcgccttatc cggtaactat cgtcttgagt   6480
```

```
ccaacccggt aagacacgac ttatcgccac tggcagcagc cactggtaac aggattagca      6540
gagcgaggta tgtaggcggt gctacagagt tcttgaagtg gtggcctaac tacggctaca      6600
ctagaaggac agtatttggt atctgcgctc tgctgaagcc agttaccttc ggaaaaagag      6660
ttggtagctc ttgatccggc aaacaaacca ccgctggtag cggtggtttt tttgtttgca      6720
agcagcagat tacgcgcaga aaaaaggat ctcaagaaga tcctttgatc ttttctacgg       6780
ggtctgacgc tcagtggaac gaaaactcac gttaagggat tttggtcatg agattatcaa      6840
aaaggatctt cacctagatc cttttaaatt aaaaatgaag ttttaaatca atctaaagta      6900
tatatgagta aacttggtct gacagttacc aatgcttaat cagtgaggca cctatctcag      6960
cgatctgtct atttcgttca tccatagttg cctgactccc cgtcgtgtag ataactacga      7020
tacgggaggg cttaccatct ggccccagtg ctgcaatgat accgcgagac ccacgctcac      7080
cggctccaga tttatcagca ataaaccagc cagccggaag ggccgagcgc agaagtggtc      7140
ctgcaacttt atccgcctcc atccagtcta ttaattgttg ccgggaagct agagtaagta      7200
gttcgccagt taatagtttg cgcaacgttg ttgccattgc tacaggcatc gtggtgtcac      7260
gctcgtcgtt tggtatggct tcattcagct ccggttccca acgatcaagg cgagttacat      7320 gatccccat gttgtgcaaa aaagcggtta gctccttcgg tcctccgatc gttgtcagaa       7380
gtaagttggc cgcagtgtta tcactcatgg ttatggcagc actgcataat tctcttactg      7440
tcatgccatc cgtaagatgc ttttctgtga ctggtgagta ctcaaccaag tcattctgag      7500
aatagtgtat gcggcgaccg agttgctctt gcccggcgtc aatacgggat aataccgcgc      7560
cacatagcag aactttaaaa gtgctcatca ttggaaaacg ttcttcgggg cgaaaactct      7620
caaggatctt accgctgttg agatccagtt cgatgtaacc cactcgtgca cccaactgat      7680
cttcagcatc ttttactttc accagcgttt ctgggtgagc aaaaacagga aggcaaaatg      7740
ccgcaaaaaa gggaataagg gcgacacgga aatgttgaat actcatactc ttcctttttc      7800
aatattattg aagcatttat cagggttatt gtctcatgag cggatacata tttgaatgta      7860
tttagaaaaa taaacaaata ggggttccgc gcacatttcc ccgaaaagtg c               7911
```

<210> SEQ ID NO 6
<211> LENGTH: 35
<212> TYPE: DNA
<213> ORGANISM: Artificial Sequence
<220> FEATURE:
<223> OTHER INFORMATION: Forward primer (A424)

<400> SEQUENCE: 6
gccagaattc gatttatgca tgttgtttac tgagc                                  35

<210> SEQ ID NO 7
<211> LENGTH: 35
<212> TYPE: DNA
<213> ORGANISM: Artificial Sequence
<220> FEATURE:
<223> OTHER INFORMATION: Reverse primer (A425)

<400> SEQUENCE: 7
gctcagtaaa caacatgcat aaatcgaatt ctggc                                  35

<210> SEQ ID NO 8
<211> LENGTH: 23
<212> TYPE: DNA
<213> ORGANISM: Artificial Sequence
<220> FEATURE:
<223> OTHER INFORMATION: Forward primer (A210)

-continued

<400> SEQUENCE: 8
cccttgaacc tcctcgttcg acc                                              23

<210> SEQ ID NO 9
<211> LENGTH: 23
<212> TYPE: DNA
<213> ORGANISM: Artificial Sequence
<220> FEATURE:
<223> OTHER INFORMATION: Reverse primer (A211)

<400> SEQUENCE: 9
gagcctgggg actttccaca ccc                                              23

<210> SEQ ID NO 10
<211> LENGTH: 20
<212> TYPE: DNA
<213> ORGANISM: Artificial Sequence
<220> FEATURE:
<223> OTHER INFORMATION: Forward primer F1 (A252)

<400> SEQUENCE: 10
gttttatctg tgcttatgcc                                                  20

<210> SEQ ID NO 11
<211> LENGTH: 19
<212> TYPE: DNA
<213> ORGANISM: Artificial Sequence
<220> FEATURE:
<223> OTHER INFORMATION: Reverse primer F1 (A253)

<400> SEQUENCE: 11
gctcgtatgt tgtgtggaa                                                   19

<210> SEQ ID NO 12
<211> LENGTH: 20
<212> TYPE: DNA
<213> ORGANISM: Artificial Sequence
<220> FEATURE:
<223> OTHER INFORMATION: Forward primer F2 (A254)

<400> SEQUENCE: 12
aaccatcacc ctaatcaagt                                                  20

<210> SEQ ID NO 13
<211> LENGTH: 18
<212> TYPE: DNA
<213> ORGANISM: Artificial Sequence
<220> FEATURE:
<223> OTHER INFORMATION: Reverse primer F2 (A255)

<400> SEQUENCE: 13
gtcgccgcat acactatt                                                    18

<210> SEQ ID NO 14
<211> LENGTH: 20
<212> TYPE: DNA
<213> ORGANISM: Artificial Sequence
<220> FEATURE:
<223> OTHER INFORMATION: Forward primer F3 (A256)

<400> SEQUENCE: 14
ttatccagtc atacagcagg                                                  20

<210> SEQ ID NO 15

```
<211> LENGTH: 20
<212> TYPE: DNA
<213> ORGANISM: Artificial Sequence
<220> FEATURE:
<223> OTHER INFORMATION: Reverse primer F3 (A257)

<400> SEQUENCE: 15
acccctgctg tatgactgga                                              20

<210> SEQ ID NO 16
<211> LENGTH: 19
<212> TYPE: DNA
<213> ORGANISM: Artificial Sequence
<220> FEATURE:
<223> OTHER INFORMATION: Forward primer F4 (A258)

<400> SEQUENCE: 16
gaccagaatg tccaccagg                                               19

<210> SEQ ID NO 17
<211> LENGTH: 20
<212> TYPE: DNA
<213> ORGANISM: Artificial Sequence
<220> FEATURE:
<223> OTHER INFORMATION: Reverse primer F4 (A259)

<400> SEQUENCE: 17
gccacctctg acttgagcgt                                              20

<210> SEQ ID NO 18
<211> LENGTH: 3891
<212> TYPE: DNA
<213> ORGANISM: Artificial Sequence
<220> FEATURE:
<223> OTHER INFORMATION: Flag-Spy1a-pTRE-Tight fusion gene fragment
      construct

<400> SEQUENCE: 18
ctcgagttta ctccctatca gtgatagaga acgtatgtcg agtttactcc ctatcagtga    60
tagagaacga tgtcgagttt actccctatc agtgatagag aacgtatgtc gagtttactc   120
cctatcagtg atagagaacg tatgtcgagt ttactcccta tcagtgatag agaacgtatg   180
tcgagtttat ccctatcagt gatagagaac gtatgtcgag tttactccct atcagtgata   240
gagaacgtat gtcgaggtag gcgtgtacgg tgggaggcct ataagcag agctcgttta    300 gtgaaccgtc agatcgcctg gagaattcgc ggccgcgtcg acctgcgacg gagccttgac   360
cgccgttgcc cggccctctc ccgcgcagcc ccgggcttcc gcaggaatat gggaaaccc   420 atatggacta caaagaccat gacggtgatt ataaagatca tgatatcgat tacaaggatg   480
acgatgacaa gaggcacaat cagatgtgtt gtgagacacc acctactgtc actgtttatg   540
taaaatcagg gtcaaataga tcacatcagc ctaaaaagcc cattactctg aagcgtccta   600
tttgtaaaga taattggcaa gcatttgaaa aaatacaca taataacaac aaatctaaac   660
gccccaaagg accttgtctg gttatacagc gtcaggatat gactgctttc tttaaattat   720
ttgatgacga tttaattcaa gatttcttgt ggatggactg ctgctgtaaa attgcagaca   780
agtatctttt ggctatgacc tttgtttatt tcaagagggc taaattact ataagtgagc   840 ataccaggat aaatttcttt attgctctgt atctggctaa tacagttgaa gaagatgaag   900 aagaaccaa gtacgaaatt tttccatggg ctttagggaa aaactggaga aaattgttcc   960
ctaatttctt aaagttaagg gaccagctct gggatagaat tgactatagg gctattgtaa  1020
```

```
gcaggcgatg ttgtgaggag gttatggcca ttgcaccaac ccattatatc tggcaaagag    1080
aacgttctgt tcatcacagt ggagctgtca gaaactacaa cagagatgaa gttcagctgc    1140
cccggggacc tagtgccaca ccagtagatt gttcactctg tggtaaaaaa agaagatatg    1200
ttagactggg attgtcttca tcatcatctt tatccagtca tacagcaggg gtgacagaaa    1260
aacattctca ggactcatac aactcactgt caatggacat aataggtgat ccttctcaag    1320
cttatactgg ttctgaaggt atgatatagt aatatgccag aattagattt atgcatgttg    1380
tttactgagc tctagtcagt cctttctggc ggggatacat aataatttat atactccaac    1440
aatatgagtt aaattaatct tgaaactttc tcccctttca gttacttttt gtcttgtgtc    1500
catatttgtt ttgtggtgac ccacctaaac agatttttaa tgtgacctat gttaagttga    1560
aaactaatgc accataagcc tcagtatttt aagagcctga atcattttt tgaaatgttt     1620
atttattca aagggtttc aagaagaaaa taaatttact tgtaatctca aaaaaaaaa       1680
aaaaaaaaaa atctagagga tcataatcag ccataccaca tttgtagagg ttttacttgc    1740
tttaaaaaac ctcccacacc tccccctgaa cctgaaacat aaaatgaatg caattgttgt    1800
tgttaacttg tttattgcag cttataatgg ttacaaataa agcaatagca tcacaaattt    1860
cacaaataaa gcatttttt cactgcctcg agcttcctcg ctcactgact cgctgcgctc     1920
ggtcgttcgg ctgcggcgag cggtatcagc tcactcaaag gcggtaatac ggttatccac    1980
agaatcaggg gataacgcag gaaagaacat gtgagcaaaa ggccagcaaa aggccaggaa    2040
ccgtaaaaag gccgcgttgc tggcgttttt ccataggctc cgcccccctg acgagcatca    2100
caaaaatcga cgctcaagtc agaggtggcg aaacccgaca ggactataaa gataccaggc    2160
gtttccccct ggaagctccc tcgtgcgctc tcctgttccg accctgccgc ttaccggata    2220
cctgtccgcc tttctccctt cgggaagcgt ggcgctttct caatgctcac gctgtaggta    2280
tctcagttcg gtgtaggtcg ttcgctccaa gctgggctgt gtgcacgaac cccccgttca    2340
gcccgaccgc tgcgccttat ccggtaacta tcgtcttgag tccaacccgg taagacacga    2400
cttatcgcca ctggcagcag ccactggtaa caggattagc agagcgaggt atgtaggcgg    2460
tgctacagag ttcttgaagt ggtggcctaa ctacggctac actagaagga cagtatttgg    2520
tatctgcgct ctgctgaagc cagttacctt cggaaaaaga gttggtagct cttgatccgg    2580
caaacaaacc accgctggta gcggtggttt ttttgtttgc aagcagcaga ttacgcgcag    2640
aaaaaaagga tctcaagaag atcctttgat cttttctacg gggtctgacg ctcagtggaa    2700
cgaaaactca cgttaaggga ttttggtcat gagattatca aaaaggatct tcacctagat    2760
ccttttaaat taaaatgaa gttttaaatc aatctaaagt atatatgagt aaacttggtc     2820
tgacagttac caatgcttaa tcagtgaggc acctatctca gcgatctgtc tatttcgttc    2880
atccatagtt gcctgactcc ccgtcgtgta gataactacg atacgggagg gcttaccatc    2940
tggccccagt gctgcaatga taccgcgaga cccacgctca ccggctccag atttatcagc    3000
aataaaccag ccagccggaa gggccgagcg cagaagtggt cctgcaactt tatccgcctc    3060
catccagtct attaattgtt gccgggaagc tagagtaagt agttcgccag ttaatagttt    3120
gcgcaacgtt gttgccattg ctacaggcat cgtggtgtca cgctcgtcgt ttggtatggc    3180
ttcattcagc tccggttccc aacgatcaag gcgagttaca tgatccccca tgttgtgcaa    3240
aaaagcggtt agctccttcg gtcctccgat cgttgtcaga agtaagttgg ccgcagtgtt    3300
atcactcatg gttatggcag cactgcataa ttctcttact gtcatgccat ccgtaagatg    3360
cttttctgtg actggtgagt actcaaccaa gtcattctga gaatagtgta tgcggcgacc    3420
```

```
gagttgctct tgcccggcgt caatacggga taataccgcg ccacatagca gaactttaaa      3480
agtgctcatc attggaaaac gttcttcggg gcgaaaactc tcaaggatct taccgctgtt      3540
gagatccagt tcgatgtaac ccactcgtgc acccaactga tcttcagcat cttttacttt      3600
caccagcgtt tctgggtgag caaaaacagg aaggcaaaat gccgcaaaaa agggaataag      3660
ggcgacacgg aaatgttgaa tactcatact cttccttttt caatattatt gaagcattta      3720
tcagggttat tgtctcatga gcggatacat atttgaatgt atttagaaaa ataaacaaat      3780
aggggttccg cgcacatttc cccgaaaagt gccacctgac gtctaagaaa ccattattat      3840
catgacatta acctataaaa ataggcgtat cacgaggccc tttcgtcttc a               3891

<210> SEQ ID NO 19
<211> LENGTH: 26
<212> TYPE: DNA
<213> ORGANISM: Artificial Sequence
<220> FEATURE:
<223> OTHER INFORMATION: Primer (A548)

<400> SEQUENCE: 19
atcagtgata gagaacgatg tcgagt                                           26

<210> SEQ ID NO 20
<211> LENGTH: 22
<212> TYPE: DNA
<213> ORGANISM: Artificial Sequence
<220> FEATURE:
<223> OTHER INFORMATION: Primer (A549)

<400> SEQUENCE: 20
ttgtgcctgt tgtcatcgtc at                                               22
```